US011712208B2

(12) United States Patent
Nye et al.

(10) Patent No.: US 11,712,208 B2
(45) Date of Patent: *Aug. 1, 2023

(54) SYSTEMS AND METHODS TO DELIVER POINT OF CARE ALERTS FOR RADIOLOGICAL FINDINGS

(71) Applicant: General Electric Company, Schenectady, NY (US)

(72) Inventors: Katelyn Rose Nye, Waukesha, WI (US); Gireesha Rao, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 34 days.

This patent is subject to a terminal disclaimer.

(21) Appl. No.: 17/063,294

(22) Filed: Oct. 5, 2020

(65) Prior Publication Data
US 2021/0015433 A1  Jan. 21, 2021

Related U.S. Application Data

(63) Continuation of application No. 15/821,161, filed on Nov. 22, 2017, now Pat. No. 10,799,189.

(51) Int. Cl.
*A61B 5/00*  (2006.01)
*A61B 6/03*  (2006.01)
(Continued)

(52) U.S. Cl.
CPC ............ *A61B 5/747* (2013.01); *A61B 5/0013* (2013.01); *A61B 6/032* (2013.01); *A61B 6/037* (2013.01);
(Continued)

(58) Field of Classification Search
CPC ....... A61B 5/747; A61B 5/0013; A61B 5/055; A61B 6/032–037; A61B 2017/00119;
(Continued)

(56) References Cited

U.S. PATENT DOCUMENTS 7,133,546 B2   11/2006   Dehmeshki et al.
7,783,094 B2    8/2010   Collins et al.
(Continued)

FOREIGN PATENT DOCUMENTS

JP   2009090054 A    4/2009
JP   2013134193 A    7/2013

OTHER PUBLICATIONS

Carestream, "Carestream's companion-view processing for improved visualization of tubes, lines, and pneumothoraces in digital, portable chest radiography", www.carestream.com, 2012, 4 pages.
(Continued)

*Primary Examiner* — Michael S Osinski
(74) *Attorney, Agent, or Firm* — Hanley, Flight and Zimmerman, LLC

(57) ABSTRACT

Apparatus, systems, and methods to deliver point of care alerts for radiological findings are disclosed. An example imaging apparatus includes an image data store, an image quality checker, and a training learning network. The example image data store is to store image data acquired using the imaging apparatus. The example image quality checker is to evaluate image data from the image data store in comparison to an image quality measure. The example trained learning network is to process the image data to identify a clinical finding in the image data, the identification of a clinical finding to trigger a notification at the imaging apparatus to notify a healthcare practitioner regarding the clinical finding and prompt a responsive action with respect to a patient associated with the image data.

20 Claims, 28 Drawing Sheets

(51) Int. Cl.
| | |
|---|---|
| *G16H 15/00* | (2018.01) |
| *G16H 30/40* | (2018.01) |
| *G16H 50/20* | (2018.01) |
| *G06T 7/00* | (2017.01) |
| *A61B 5/055* | (2006.01) |
| *A61B 6/00* | (2006.01) |

(52) U.S. Cl.
CPC .............. *G16H 15/00* (2018.01); *G16H 30/40* (2018.01); *G16H 50/20* (2018.01); *A61B 5/0035* (2013.01); *A61B 5/055* (2013.01); *A61B 6/467* (2013.01); *G06T 7/0012* (2013.01)

(58) Field of Classification Search
CPC ......... A61B 2017/00199; G16H 15/00; G16H 50/20; G16H 30/40; G16H 10/60; G06F 19/321; G06F 19/00; G06T 7/0012; G06T 2207/10081; G06T 2207/30004; G06T 2207/10088; G06T 2207/10116; G06T 2207/20084
See application file for complete search history.

(56) References Cited

U.S. PATENT DOCUMENTS

| | | | |
|---|---|---|---|
| 8,526,693 | B2 | 9/2013 | Vijaykalyan et al. |
| 8,923,580 | B2 | 12/2014 | Dekel et al. |
| 9,014,485 | B2 | 4/2015 | Moehrle |
| 9,519,866 | B2 | 12/2016 | Kawagishi et al. |
| 9,805,470 | B2 | 10/2017 | Bhatia et al. |
| 9,846,938 | B2 | 12/2017 | Steigauf et al. |
| 10,169,863 | B2 | 1/2019 | Reicher et al. |
| 10,307,051 | B2* | 6/2019 | Ootsuki ................ A61B 3/102 |
| 10,347,010 | B2 | 7/2019 | Risman et al. |
| 10,387,765 | B2* | 8/2019 | Mailhe .................... G06N 3/02 |
| 10,504,027 | B1 | 12/2019 | Kim et al. |
| 10,783,634 | B2 | 9/2020 | Nye et al. |
| 11,594,310 | B1* | 2/2023 | Bradley ................ G06N 20/00 |
| 2004/0111299 | A1 | 6/2004 | Onishi |
| 2005/0049497 | A1 | 3/2005 | Krishnan et al. |
| 2005/0078857 | A1 | 4/2005 | Park |
| 2006/0173715 | A1 | 8/2006 | Wang |
| 2006/0274928 | A1 | 12/2006 | Collins et al. |
| 2007/0292012 | A1 | 12/2007 | Brandon et al. |
| 2008/0025583 | A1 | 1/2008 | Jabri et al. |
| 2008/0118128 | A1* | 5/2008 | Toth ..................... G06T 11/003 <br> 382/131 |
| 2008/0139920 | A1 | 6/2008 | Biglieri et al. |
| 2008/0215630 | A1 | 9/2008 | Oosawa et al. |
| 2009/0116713 | A1 | 5/2009 | Yan |
| 2009/0172036 | A1 | 7/2009 | Marx |
| 2009/0192824 | A1 | 7/2009 | Minakuchi et al. |
| 2009/0204436 | A1 | 8/2009 | Thorne et al. |
| 2010/0082506 | A1 | 4/2010 | Gopal |
| 2010/0114597 | A1 | 5/2010 | Shreiber et al. |
| 2010/0189322 | A1 | 7/2010 | Sakagawa |
| 2010/0256459 | A1 | 10/2010 | Miyasa et al. |
| 2010/0280842 | A1 | 11/2010 | Iwase et al. |
| 2011/0110572 | A1 | 5/2011 | Guehring et al. |
| 2012/0134555 | A1 | 5/2012 | Iizuka et al. |
| 2012/0183187 | A1 | 7/2012 | Sasaki |
| 2012/0250961 | A1 | 10/2012 | Iwasaki |
| 2013/0039552 | A1* | 2/2013 | Becker .................... G06F 16/51 <br> 382/128 |
| 2013/0114867 | A1 | 5/2013 | Kondo et al. |
| 2013/0136312 | A1 | 5/2013 | Tseng et al. |
| 2013/0150700 | A1 | 6/2013 | Kalvesten et al. |
| 2015/0030239 | A1 | 1/2015 | Fang |
| 2015/0199478 | A1 | 7/2015 | Bhatia et al. |
| 2016/0063397 | A1 | 3/2016 | Ylipaavalniemi et al. |
| 2016/0106347 | A1 | 4/2016 | Patwardhan et al. |
| 2016/0110904 | A1 | 4/2016 | Jeon et al. |
| 2016/0203263 | A1* | 7/2016 | Maier .................... G16H 30/40 <br> 705/2 |
| 2016/0292844 | A1 | 10/2016 | Karube |
| 2016/0300120 | A1 | 10/2016 | Haas et al. |
| 2016/0335764 | A1* | 11/2016 | Kawagishi ............. G16H 70/60 |
| 2016/0350919 | A1 | 12/2016 | Steigauf |
| 2016/0364539 | A1* | 12/2016 | Reicher ................. G06F 40/169 |
| 2016/0364862 | A1 | 12/2016 | Reicher et al. |
| 2017/0032241 | A1 | 2/2017 | Corrado et al. |
| 2017/0071573 | A1 | 3/2017 | Takahashi |
| 2017/0091930 | A1 | 3/2017 | Kozuka et al. |
| 2017/0215832 | A1* | 8/2017 | Nagano .................... A61B 6/46 |
| 2017/0319150 | A1* | 11/2017 | Goto ..................... G16H 30/40 |
| 2017/0323064 | A1* | 11/2017 | Bates .................... G16H 50/20 |
| 2017/0337682 | A1 | 11/2017 | Liao et al. |
| 2017/0337687 | A1 | 11/2017 | Wang et al. |
| 2018/0008139 | A1 | 1/2018 | Ootsuki |
| 2018/0225993 | A1 | 8/2018 | Buras et al. |
| 2018/0232603 | A1 | 8/2018 | Shim et al. |
| 2018/0247107 | A1 | 8/2018 | Murthy et al. |
| 2018/0276498 | A1 | 9/2018 | Madabhushi et al. |
| 2018/0307749 | A1 | 10/2018 | Al Hasan et al. |
| 2018/0330058 | A1 | 11/2018 | Bates |
| 2019/0008480 | A1 | 1/2019 | Gerard et al. |
| 2019/0038148 | A1* | 2/2019 | Valys ................... A61B 5/7275 |
| 2019/0080454 | A1 | 3/2019 | Hameed et al. |
| 2019/0147346 | A1 | 5/2019 | Reicher et al. |
| 2019/0147620 | A1* | 5/2019 | Pinel ........................ G06F 9/00 <br> 382/159 |
| 2019/0150857 | A1 | 5/2019 | Nye et al. |
| 2019/0156937 | A1 | 5/2019 | Shimomura et al. |
| 2019/0156942 | A1* | 5/2019 | Pronk .................... G16H 30/20 |
| 2019/0159762 | A1 | 5/2019 | Li |
| 2019/0164284 | A1 | 5/2019 | Nye et al. |
| 2019/0164285 | A1 | 5/2019 | Nye et al. |
| 2019/0172205 | A1 | 6/2019 | Mao et al. |
| 2019/0198172 | A1 | 6/2019 | Nelson, Jr. |
| 2019/0290102 | A1* | 9/2019 | Sasaki ................ A61B 1/00066 |
| 2019/0341147 | A1 | 11/2019 | Lord et al. |
| 2020/0008751 | A1 | 1/2020 | Kano et al. |
| 2020/0058390 | A1 | 2/2020 | Kohle et al. |
| 2020/0175684 | A1* | 6/2020 | Podilchuk ............. G06T 7/0016 |

OTHER PUBLICATIONS

United States Patent and Trademark Office, "Advisory action," issued in connection with U.S. Appl. No. 15/821,161, dated Apr. 20, 2020, 5 pages.

United States Patent and Trademark Office, "Final office action," issued in connection with U.S. Appl. No. 15/821,161, dated Feb. 10, 2020, 18 pages.

United States Patent and Trademark Office, "Non-Final office action," issued in connection with U.S. Appl. No. 15/821,161, dated Oct. 22, 2019, 35 pages.

United States Patent and Trademark Office, "Notice of Allowance," issued in connection with U.S. Appl. No. 15/821,161, dated May 20, 2020, 11 pages.

European Patent Office, "Extended Search Report," issued in connection with EP patent application No. 18206181.2, dated Apr. 23, 2019, 9 pages.

United States Patent and Trademark Office, "Notice of Allowance," issued in connection with U.S. Appl. No. 16/196,953, dated May 12, 2020, 20 pages.

United States Patent and Trademark Office, "Non-Final Office action" issued in connection with U.S. Appl. No. 16/196,943, dated Jul. 13, 2020, 20 pages.

European Patent Office, "Communication pursuant to Article 94(3)EPC," issued in connection with European patent application No. 18 206 181.2, dated Oct. 7, 2020, 5 pages.

JP application 2018-216265 filed Nov. 19, 2018—Office Action dated Dec. 21, 2021; Machine Translation, 6 pages.

JP2009-090054 Abstract; English translation obtained from Espacenet. com Feb. 22, 2022.

JP patent application 2018-216265 filed Nov. 19, 2018—Office Action dated Jul. 27, 2022, Machine Translation, 4 pages.

(56) References Cited

OTHER PUBLICATIONS

JP2013134193 English Abstract, Espacenet—search results Nov. 1, 2022; 1 page.

* cited by examiner

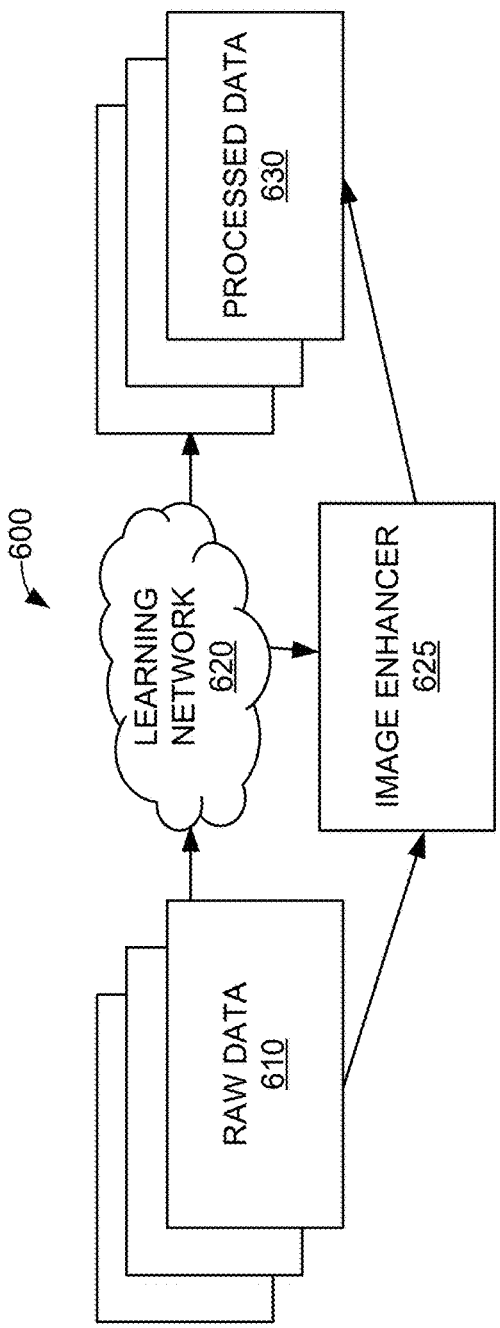
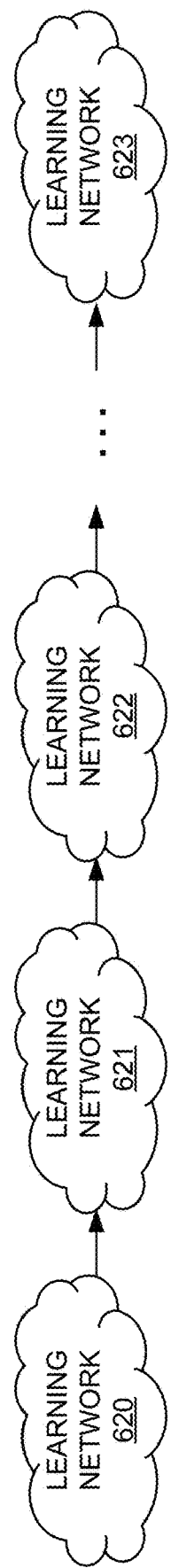
FIG. 6A
FIG. 6B

FIG. 23

SYSTEMS AND METHODS TO DELIVER POINT OF CARE ALERTS FOR RADIOLOGICAL FINDINGS

CROSS-REFERENCE TO RELATED APPLICATION

This patent arises from U.S. Non-Provisional patent application Ser. No. 15/821,161, which was filed on Nov. 22, 2017 (now U.S. Pat. No. 10,799,189). U.S. Non-Provisional patent application Ser. No. 15/821,161 is hereby incorporated herein by reference in its entirety. Priority to U.S. Non-Provisional patent application Ser. No. 15/821,161 is hereby claimed.

FIELD OF THE DISCLOSURE

This disclosure relates generally to improved medical systems and, more particularly, to improved learning systems and methods for medical image processing.

BACKGROUND

A variety of economy, operational, technological, and administrative hurdles challenge healthcare facilities, such as hospitals, clinics, doctors' offices, imaging centers, teleradiology, etc., to provide quality care to patients. Economic drivers, less skilled staff, fewer staff, complicated equipment, and emerging accreditation for controlling and standardizing radiation exposure dose usage across a healthcare enterprise create difficulties for effective management and use of imaging and information systems for examination, diagnosis, and treatment of patients.

Healthcare provider consolidations create geographically distributed hospital networks in which physical contact with systems is too costly. At the same time, referring physicians want more direct access to supporting data in reports along with better channels for collaboration. Physicians have more patients, less time, and are inundated with huge amounts of data, and they are eager for assistance.

Healthcare provider (e.g., x-ray technologist, doctor, nurse, etc.) tasks including image processing and analysis, quality assurance/quality control, etc., are time consuming and resource intensive tasks impractical, if not impossible, for humans to accomplish alone.

BRIEF SUMMARY

Certain examples provide apparatus, systems, and methods to improve imaging quality control, image processing, identification of findings in image data, and generation of notification at or near a point of care for a patient.

Certain examples provide an imaging apparatus including an image data store, an image quality checker, and a trained learning network. The example image data store is to store image data acquired using the imaging apparatus. The example image quality checker is to evaluate image data from the image data store in comparison to an image quality measure. The example trained learning network is to process the image data to identify a clinical finding in the image data, the identification of a clinical finding to trigger a notification at the imaging apparatus to notify a healthcare practitioner regarding the clinical finding and prompt a responsive action with respect to a patient associated with the image data.

Certain examples provide a computer-readable storage medium in an imaging apparatus including instructions which, when executed, cause a processor in the imaging apparatus to implement at least an image data store to store image data acquired using the imaging apparatus. The example instructions, when executed, cause the processor to implement an image quality checker to evaluate image data from the image data store in comparison to an image quality measure. The example instructions, when executed, cause the processor to implement/execute a trained learning network to process the image data to identify a clinical finding in the image data, the identification of a clinical finding to trigger a notification at the imaging apparatus to notify a healthcare practitioner regarding the clinical finding and prompt a responsive action with respect to a patient associated with the image data.

Certain examples provide a computer-implemented method including evaluating, at a mobile imaging apparatus, image data acquired using the image apparatus in comparison to an image quality measure. The example method includes, when the image data satisfies the image quality measure, processing the image data via a learning network to identify a clinical finding in the image data. The example method includes triggering, based on identification of a clinical finding, an alert at the imaging apparatus to notify a healthcare practitioner regarding the clinical finding and prompt a responsive action with respect to a patient associated with the image data.

BRIEF DESCRIPTION OF THE DRAWINGS

FIG. 6A illustrates an example configuration to apply a learning network to process and/or otherwise evaluate an image.

FIG. 6B illustrates a combination of a plurality of learning networks.

FIGS. 13-24 illustrate example displays to provide output and facilitate interaction in accordance with the apparatus, systems, and methods described above in connection with FIGS. 1-12.

Figure 1A:
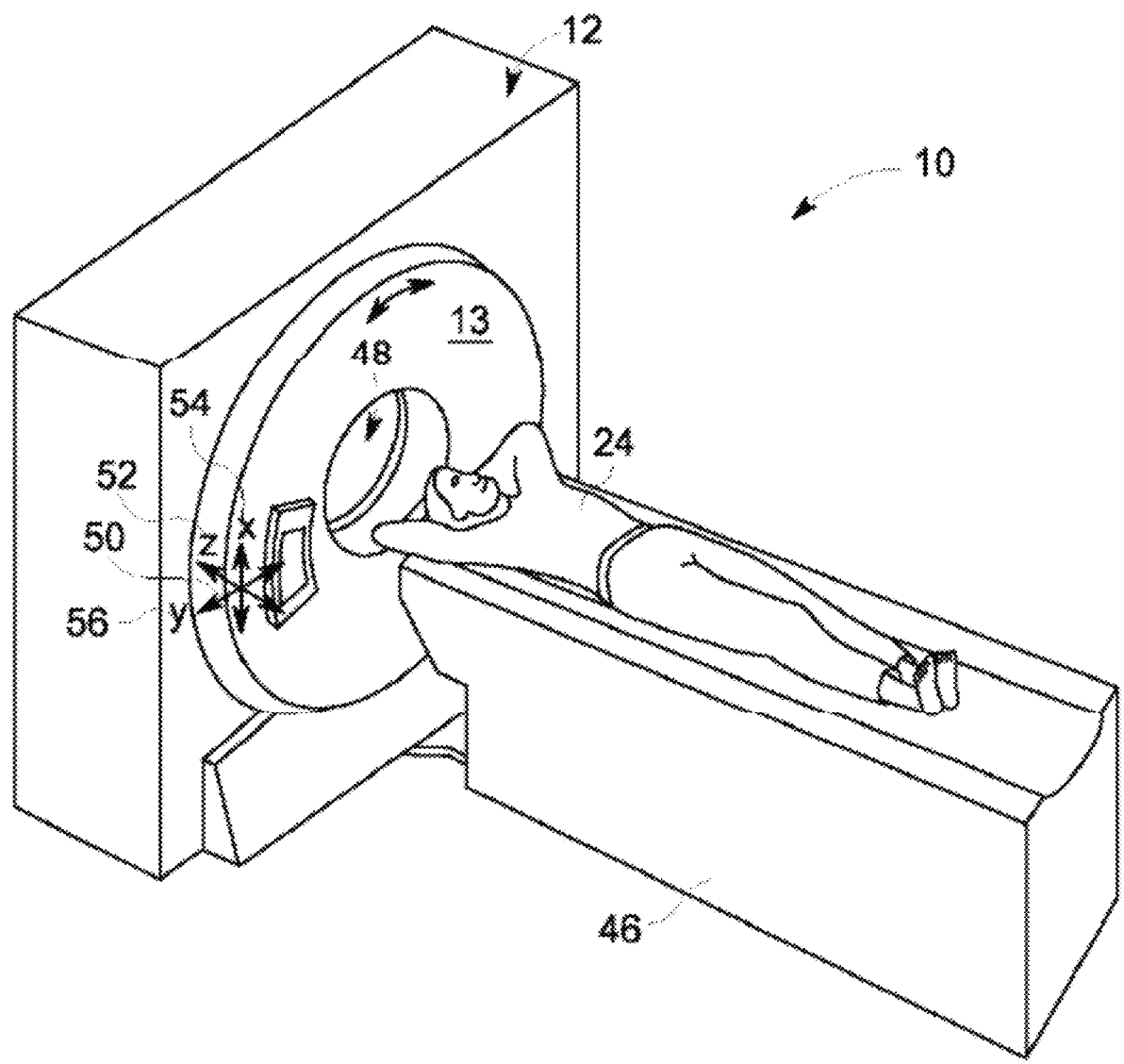
FIGS. 1A-1B illustrate an example imaging system to which the methods, apparatus, and articles of manufacture disclosed herein can be applied.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings. The figures are not scale. Wherever possible, the same reference numbers will be used throughout the drawings and accompanying written description to refer to the same or like parts.

DETAILED DESCRIPTION

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

While certain examples are described below in the context of medical or healthcare systems, other examples can be implemented outside the medical environment. For example, certain examples can be applied to non-medical imaging such as non-destructive testing, explosive detection, etc.

I. OVERVIEW

Imaging devices (e.g., gamma camera, positron emission tomography (PET) scanner, computed tomography (CT) scanner, X-Ray machine, fluoroscopy machine, magnetic resonance (MR) imaging machine, ultrasound scanner, etc.) generate medical images (e.g., native Digital Imaging and Communications in Medicine (DICOM) images) representative of the parts of the body (e.g., organs, tissues, etc.) to diagnose and/or treat diseases. Medical images may include volumetric data including voxels associated with the part of the body captured in the medical image. Medical image visualization software allows a clinician to segment, annotate, measure, and/or report functional or anatomical characteristics on various locations of a medical image. In some examples, a clinician may utilize the medical image visualization software to identify regions of interest with the medical image.

Acquisition, processing, quality control, analysis, and storage of medical image data play an important role in diagnosis and treatment of patients in a healthcare environment. A medical imaging workflow and devices involved in the workflow can be configured, monitored, and updated throughout operation of the medical imaging workflow and devices. Machine and/or deep learning can be used to help configure, monitor, and update the medical imaging workflow and devices.

Certain examples provide and/or facilitate improved imaging devices which improve diagnostic accuracy and/or coverage. Certain examples facilitate improved image reconstruction and further processing to provide improved diagnostic accuracy.

Machine learning techniques, whether deep learning networks or other experiential/observational learning system, can be used to locate an object in an image, understand speech and convert speech into text, and improve the relevance of search engine results, for example. Deep learning is a subset of machine learning that uses a set of algorithms to model high-level abstractions in data using a deep graph with multiple processing layers including linear and non-linear transformations. While many machine learning systems are seeded with initial features and/or network weights to be modified through learning and updating of the machine learning network, a deep learning network trains itself to identify "good" features for analysis. Using a multilayered architecture, machines employing deep learning techniques can process raw data better than machines using conventional machine learning techniques. Examining data for groups of highly correlated values or distinctive themes is facilitated using different layers of evaluation or abstraction.

Throughout the specification and claims, the following terms take the meanings explicitly associated herein, unless the context clearly dictates otherwise. The term "deep learning" is a machine learning technique that utilizes multiple data processing layers to recognize various structures in data sets and classify the data sets with high accuracy. A deep learning network can be a training network (e.g., a training network model or device) that learns patterns based on a plurality of inputs and outputs. A deep learning network can be a deployed network (e.g., a deployed network model or device) that is generated from the training network and provides an output in response to an input.

The term "supervised learning" is a deep learning training method in which the machine is provided already classified data from human sources. The term "unsupervised learning" is a deep learning training method in which the machine is not given already classified data but makes the machine useful for abnormality detection. The term "semi-supervised learning" is a deep learning training method in which the machine is provided a small amount of classified data from human sources compared to a larger amount of unclassified data available to the machine.

The term "representation learning" is a field of methods for transforming raw data into a representation or feature that can be exploited in machine learning tasks. In supervised learning, features are learned via labeled input.

The term "convolutional neural networks" or "CNNs" are biologically inspired networks of interconnected data used in deep learning for detection, segmentation, and recognition of pertinent objects and regions in datasets. CNNs evaluate raw data in the form of multiple arrays, breaking the data in a series of stages, examining the data for learned features.

The term "transfer learning" is a process of a machine storing the information used in properly or improperly solving one problem to solve another problem of the same or similar nature as the first. Transfer learning may also be known as "inductive learning". Transfer learning can make use of data from previous tasks, for example.

The term "active learning" is a process of machine learning in which the machine selects a set of examples for which to receive training data, rather than passively receiving examples chosen by an external entity. For example, as a machine learns, the machine can be allowed to select examples that the machine determines will be most helpful for learning, rather than relying only an external human expert or external system to identify and provide examples.

The term "computer aided detection" or "computer aided diagnosis" refer to computers that analyze medical images for the purpose of suggesting a possible diagnosis.

Certain examples use neural networks and/or other machine learning to implement a new workflow for image and associated patient analysis including generating alerts based on radiological findings may be generated and delivered at the point of care of a radiology exam. Certain examples use Artificial Intelligence (AI) algorithms to immediately (e.g., with a data processing, transmission, and/or storage/retrieval latency) process a radiological exam (e.g., an image or set of images), and provide an alert based on the automated exam analysis at the point of care. The alert and/or other notification can be seen on a visual display, represented by a sensor (e.g., light color, etc.), be an audible noise/tone, and/or be sent as a message (e.g., short messaging service (SMS), Health Level 7 (HL7), DICOM header tag, phone call, etc.). The alerts may be intended for the technologist acquiring the exam, clinical team providers (e.g., nurse, doctor, etc.), radiologist, administration, operations, and/or even the patient. The alerts may be to indicate a specific or multiple quality control and/or radiological finding(s) or lack thereof in the exam image data, for example.

In certain examples, the AI algorithm can be (1) embedded within the radiology system, (2) running on a mobile device (e.g., a tablet, smart phone, laptop, other handheld or mobile computing device, etc.), and/or (3) running in a cloud (e.g., on premise or off premise) and delivers the alert via a web browser (e.g., which may appear on the radiology system, mobile device, computer, etc.). Such configurations can be vendor neutral and compatible with legacy imaging systems. For example, if the AI processor is running on a mobile device and/or in the "cloud", the configuration can receive the images (A) from the x-ray and/or other imaging system directly (e.g., set up as secondary push destination such as a Digital Imaging and Communications in Medicine (DICOM) node, etc.), (B) by tapping into a Picture Archiving and Communication System (PACS) destination for redundant image access, (C) by retrieving image data via a sniffer methodology (e.g., to pull a DICOM image off the system once it is generated), etc.

Deep Learning and Other Machine Learning

Deep learning is a class of machine learning techniques employing representation learning methods that allows a machine to be given raw data and determine the representations needed for data classification. Deep learning ascertains structure in data sets using backpropagation algorithms which are used to alter internal parameters (e.g., node weights) of the deep learning machine. Deep learning machines can utilize a variety of multilayer architectures and algorithms. While machine learning, for example, involves an identification of features to be used in training the network, deep learning processes raw data to identify features of interest without the external identification.

Deep learning in a neural network environment includes numerous interconnected nodes referred to as neurons. Input neurons, activated from an outside source, activate other neurons based on connections to those other neurons which are governed by the machine parameters. A neural network behaves in a certain manner based on its own parameters. Learning refines the machine parameters, and, by extension, the connections between neurons in the network, such that the neural network behaves in a desired manner.

Deep learning that utilizes a convolutional neural network segments data using convolutional filters to locate and identify learned, observable features in the data. Each filter or layer of the CNN architecture transforms the input data to increase the selectivity and invariance of the data. This abstraction of the data allows the machine to focus on the features in the data it is attempting to classify and ignore irrelevant background information.

Deep learning operates on the understanding that many datasets include high level features which include low level features. While examining an image, for example, rather than looking for an object, it is more efficient to look for edges which form motifs which form parts, which form the object being sought. These hierarchies of features can be found in many different forms of data such as speech and text, etc.

Learned observable features include objects and quantifiable regularities learned by the machine during supervised learning. A machine provided with a large set of well classified data is better equipped to distinguish and extract the features pertinent to successful classification of new data.

A deep learning machine that utilizes transfer learning may properly connect data features to certain classifications affirmed by a human expert. Conversely, the same machine can, when informed of an incorrect classification by a human expert, update the parameters for classification. Settings and/or other configuration information, for example, can be guided by learned use of settings and/or other configuration information, and, as a system is used more (e.g., repeatedly and/or by multiple users), a number of variations and/or other possibilities for settings and/or other configuration information can be reduced for a given situation.

An example deep learning neural network can be trained on a set of expert classified data, classified and further annotated for object localization, for example. This set of data builds the first parameters for the neural network, and this would be the stage of supervised learning. During the stage of supervised learning, the neural network can be tested whether the desired behavior has been achieved.

Once a desired neural network behavior has been achieved (e.g., a machine has been trained to operate according to a specified threshold, etc.), the machine can be deployed for use (e.g., testing the machine with "real" data, etc.). During operation, neural network classifications can be confirmed or denied (e.g., by an expert user, expert system, reference database, etc.) to continue to improve neural network behavior. The example neural network is then in a state of transfer learning, as parameters for classification that determine neural network behavior are updated based on ongoing interactions. In certain examples, the neural network can provide direct feedback to another process. In certain examples, the neural network outputs data that is buffered (e.g., via the cloud, etc.) and validated before it is provided to another process.

Deep learning machines using convolutional neural networks (CNNs) can be used for image analysis. Stages of CNN analysis can be used for facial recognition in natural images, computer-aided diagnosis (CAD), etc.

High quality medical image data can be acquired using one or more imaging modalities, such as x-ray, computed tomography (CT), molecular imaging and computed tomography (MICT), magnetic resonance imaging (MRI), etc. Medical image quality is often not affected by the machines producing the image but the patient. A patient moving during an MRI can create a blurry or distorted image that can prevent accurate diagnosis, for example.

Interpretation of medical images, regardless of quality, is only a recent development. Medical images are largely interpreted by physicians, but these interpretations can be subjective, affected by the condition of the physician's experience in the field and/or fatigue. Image analysis via machine learning can support a healthcare practitioner's workflow.

Deep learning machines can provide computer aided detection support to improve their image analysis with respect to image quality and classification, for example. However, issues facing deep learning machines applied to the medical field often lead to numerous false classifications. Deep learning machines must overcome small training datasets and require repetitive adjustments, for example.

Deep learning machines, with minimal training, can be used to determine the quality of a medical image, for example. Semi-supervised and unsupervised deep learning machines can be used to quantitatively measure qualitative aspects of images. For example, deep learning machines can be utilized after an image has been acquired to determine if the quality of the image is sufficient for diagnosis. Supervised deep learning machines can also be used for computer aided diagnosis. Supervised learning can help reduce susceptibility to false classification, for example.

Deep learning machines can utilize transfer learning when interacting with physicians to counteract the small dataset available in the supervised training. These deep learning machines can improve their computer aided diagnosis over time through training and transfer learning.

II. DESCRIPTION OF EXAMPLES

Example Imaging Systems

Figure 1B:
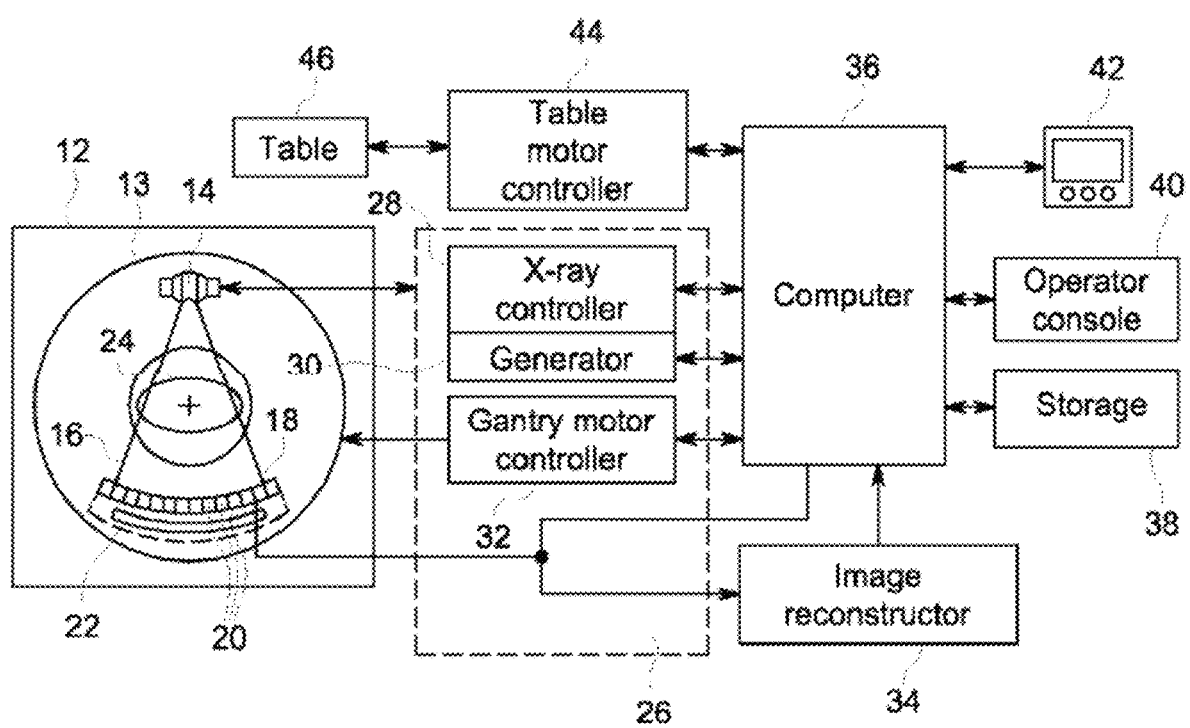

The methods, apparatus, and articles of manufacture described herein can be applied to a variety of healthcare and non-healthcare systems. In one particular example, the methods, apparatus, and articles of manufacture described herein can be applied to the components, configuration, and operation of a computed tomography (CT) imaging system. FIGS. 1A-1B illustrate an example implementation of a CT imaging scanner to which the methods, apparatus, and articles of manufacture disclosed herein can be applied. FIGS. 1A and 1B show a CT imaging system 10 including a gantry 12. Gantry 12 has a rotary member 13 with an x-ray source 14 that projects a beam of x-rays 16 toward a detector assembly 18 on the opposite side of the rotary member 13. A main bearing may be utilized to attach the rotary member 13 to the stationary structure of the gantry 12. X-ray source 14 includes either a stationary target or a rotating target. Detector assembly 18 is formed by a plurality of detectors 20 and data acquisition systems (DAS) 22, and can include a collimator. The plurality of detectors 20 sense the projected x-rays that pass through a subject 24, and DAS 22 converts the data to digital signals for subsequent processing. Each detector 20 produces an analog or digital electrical signal that represents the intensity of an impinging x-ray beam and hence the attenuated beam as it passes through subject 24. During a scan to acquire x-ray projection data, rotary member 13 and the components mounted thereon can rotate about a center of rotation.

Rotation of rotary member 13 and the operation of x-ray source 14 are governed by a control mechanism 26 of CT system 10. Control mechanism 26 can include an x-ray controller 28 and generator 30 that provides power and timing signals to x-ray source 14 and a gantry motor controller 32 that controls the rotational speed and position of rotary member 13. An image reconstructor 34 receives sampled and digitized x-ray data from DAS 22 and performs high speed image reconstruction. The reconstructed image is output to a computer 36 which stores the image in a computer storage device 38.

Computer 36 also receives commands and scanning parameters from an operator via operator console 40 that has some form of operator interface, such as a keyboard, mouse, touch sensitive controller, voice activated controller, or any other suitable input apparatus. Display 42 allows the operator to observe the reconstructed image and other data from computer 36. The operator supplied commands and parameters are used by computer 36 to provide control signals and information to DAS 22, x-ray controller 28, and gantry motor controller 32. In addition, computer 36 operates a table motor controller 44 which controls a motorized table 46 to position subject 24 and gantry 12. Particularly, table 46 moves a subject 24 through a gantry opening 48, or bore, in whole or in part. A coordinate system 50 defines a patient or Z-axis 52 along which subject 24 is moved in and out of opening 48, a gantry circumferential or X-axis 54 along which detector assembly 18 passes, and a Y-axis 56 that passes along a direction from a focal spot of x-ray tube 14 to detector assembly 18.

Thus, certain examples can apply machine learning techniques to configuration and/or operation of the CT scanner 10 and its gantry 12, rotary member 13, x-ray source 14, detector assembly 18, control mechanism 26, image reconstructor 34, computer 36, operator console 40, display 42, table controller 44, table 46, and/or gantry opening 48, etc. Component configuration, operation, etc., can be monitored based on input, desired output, actual output, etc., to learn and suggest change(s) to configuration, operation, and/or image capture and/or processing of the scanner 10 and/or its components, for example.

Figure 2:
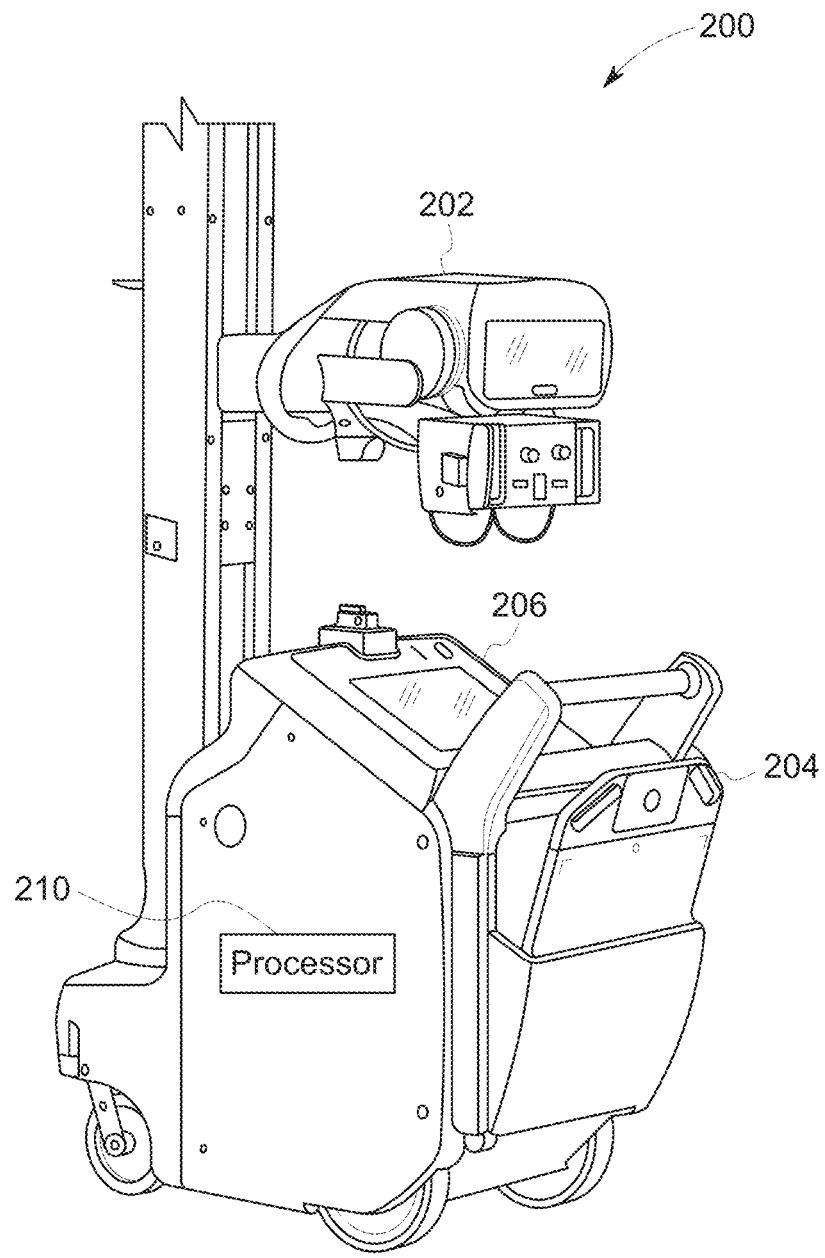
FIG. 2 illustrates an example mobile imaging system.

FIG. 2 illustrates a portable variant of an x-ray imaging system 200. The example digital mobile x-ray system 200 can be positioned with respect to a patient bed without requiring the patient to move and reposition themselves on the patient table 46 of a stationary imaging system 10. Wireless technology enables wireless communication (e.g., with adaptive, automatic channel switching, etc.) for image and/or other data transfer to and from the mobile imaging system 200. Digital images can be obtained and analyzed at the imaging system 200 and/or transferred to another system (e.g., a PACS, etc.) for further analysis, annotation, storage, etc.

The mobile imaging system 200 includes a source 202 and a wireless detector 204 that can be positioned underneath and/or otherwise with respect to a patient anatomy to be imaged. The example mobile system 200 also includes a display 206 to display results of image acquisition from the wireless detector 204. The example mobile system 200 includes a processor 210 to configure and control image acquisition, image processing, image data transmission, etc.

In some examples, the imaging system 10, 200 can include a computer and/or other processor 36, 210 to process obtained image data at the imaging system 10, 200. For example, the computer and/or other processor 36, 210 can implement an artificial neural network and/or other machine learning construct to process acquired image data and output an analysis, alert, and/or other result.

Example Learning Network Systems

Figure 3:
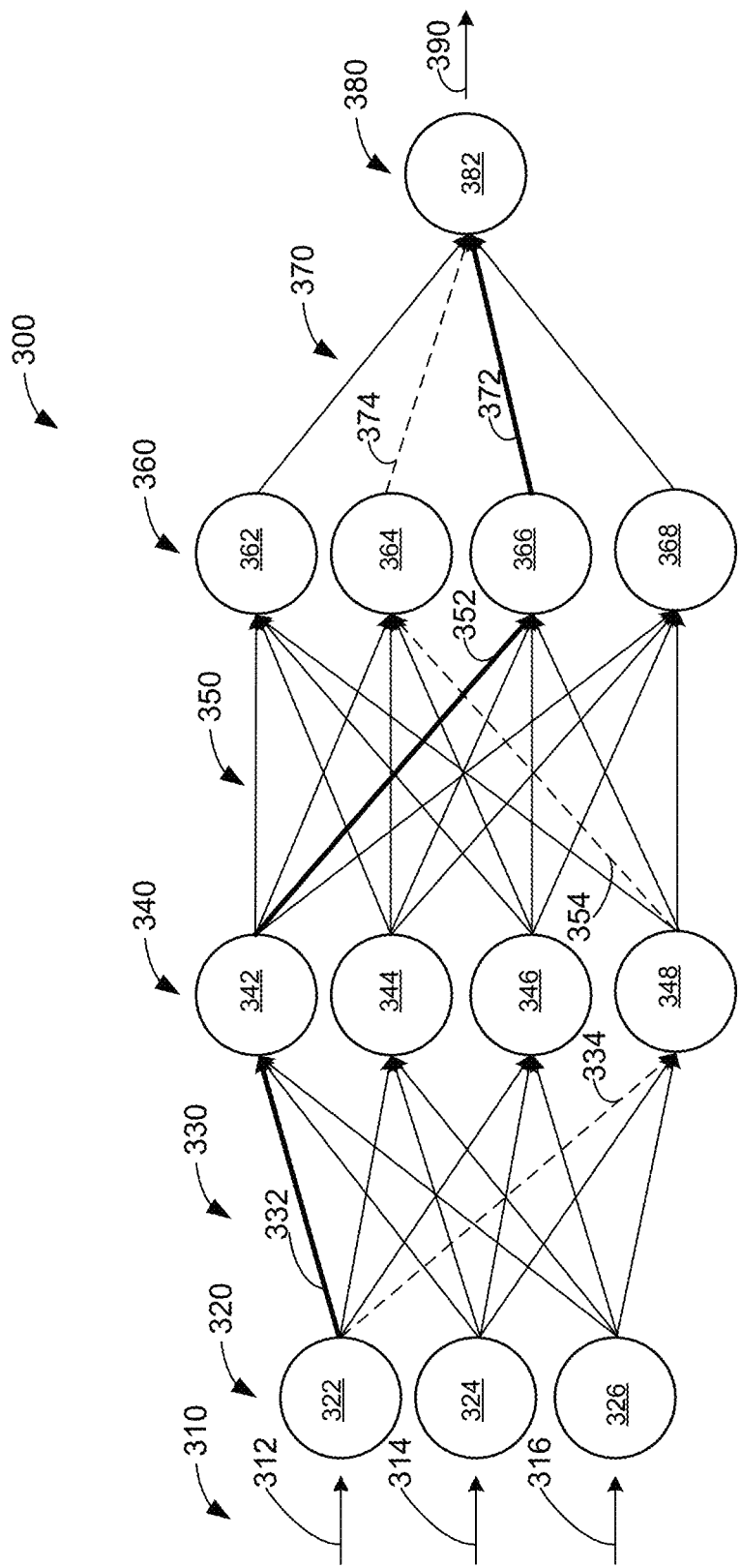
FIG. 3 is a representation of an example learning neural network.

FIG. 3 is a representation of an example learning neural network 300. The example neural network 300 includes layers 320, 340, 360, and 380. The layers 320 and 340 are connected with neural connections 330. The layers 340 and 360 are connected with neural connections 350. The layers 360 and 380 are connected with neural connections 370. Data flows forward via inputs 312, 314, 316 from the input layer 320 to the output layer 380 and to an output 390.

The layer 320 is an input layer that, in the example of FIG. 3, includes a plurality of nodes 322, 324, 326. The layers 340 and 360 are hidden layers and include, the example of FIG. 3, nodes 342, 344, 346, 348, 362, 364, 366, 368. The neural network 300 may include more or less hidden layers 340 and 360 than shown. The layer 380 is an output layer and includes, in the example of FIG. 3, a node 382 with an output 390. Each input 312-316 corresponds to a node 322-326 of the input layer 320, and each node 322-326 of the input layer 320 has a connection 330 to each node 342-348 of the hidden layer 340. Each node 342-348 of the hidden layer 340 has a connection 350 to each node 362-368 of the hidden layer 360. Each node 362-368 of the hidden layer 360 has a connection 370 to the output layer 380. The output layer 380 has an output 390 to provide an output from the example neural network 300.

Of connections 330, 350, and 370 certain example connections 332, 352, 372 may be given added weight while other example connections 334, 354, 374 may be given less weight in the neural network 300. Input nodes 322-326 are activated through receipt of input data via inputs 312-316, for example. Nodes 342-348 and 362-368 of hidden layers 340 and 360 are activated through the forward flow of data through the network 300 via the connections 330 and 350, respectively. Node 382 of the output layer 380 is activated after data processed in hidden layers 340 and 360 is sent via connections 370. When the output node 382 of the output layer 380 is activated, the node 382 outputs an appropriate value based on processing accomplished in hidden layers 340 and 360 of the neural network 300.

Figure 4:
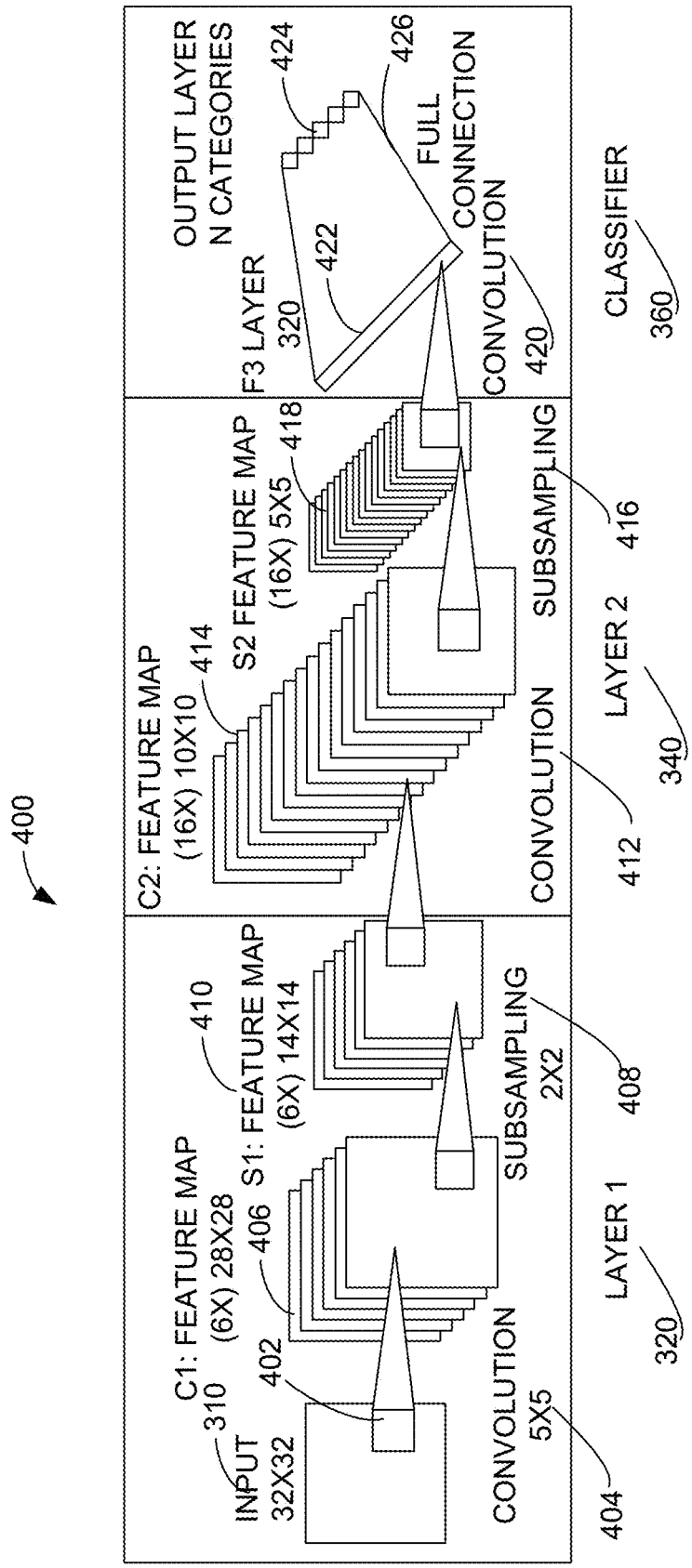
FIG. 4 illustrates a particular implementation of the example neural network as a convolutional neural network.

FIG. 4 illustrates a particular implementation of the example neural network 300 as a convolutional neural network 400. As shown in the example of FIG. 4, an input 310 is provided to the first layer 320 which processes and propagates the input 310 to the second layer 340. The input 310 is further processed in the second layer 340 and propagated to the third layer 360. The third layer 360 categorizes data to be provided to the output layer e80. More specifically, as shown in the example of FIG. 4, a convolution 404 (e.g., a 5×5 convolution, etc.) is applied to a portion or window (also referred to as a "receptive field") 402 of the input 310 (e.g., a 32×32 data input, etc.) in the first layer 320 to provide a feature map 406 (e.g., a (6×) 28×28 feature map, etc.). The convolution 404 maps the elements from the input 310 to the feature map 406. The first layer 320 also provides subsampling (e.g., 2×2 subsampling, etc.) to generate a reduced feature map 410 (e.g., a (6×) 14×14 feature map, etc.). The feature map 410 undergoes a convolution 412 and is propagated from the first layer 320 to the second layer 340, where the feature map 410 becomes an expanded feature map 414 (e.g., a (16×) 10×10 feature map, etc.). After subsampling 416 in the second layer 340, the feature map 414 becomes a reduced feature map 418 (e.g., a (16×) 4×5 feature map, etc.). The feature map 418 undergoes a convolution 420 and is propagated to the third layer 360, where the feature map 418 becomes a classification layer 422 forming an output layer of N categories 424 with connection 426 to the convoluted layer 422, for example.

Figure 5:
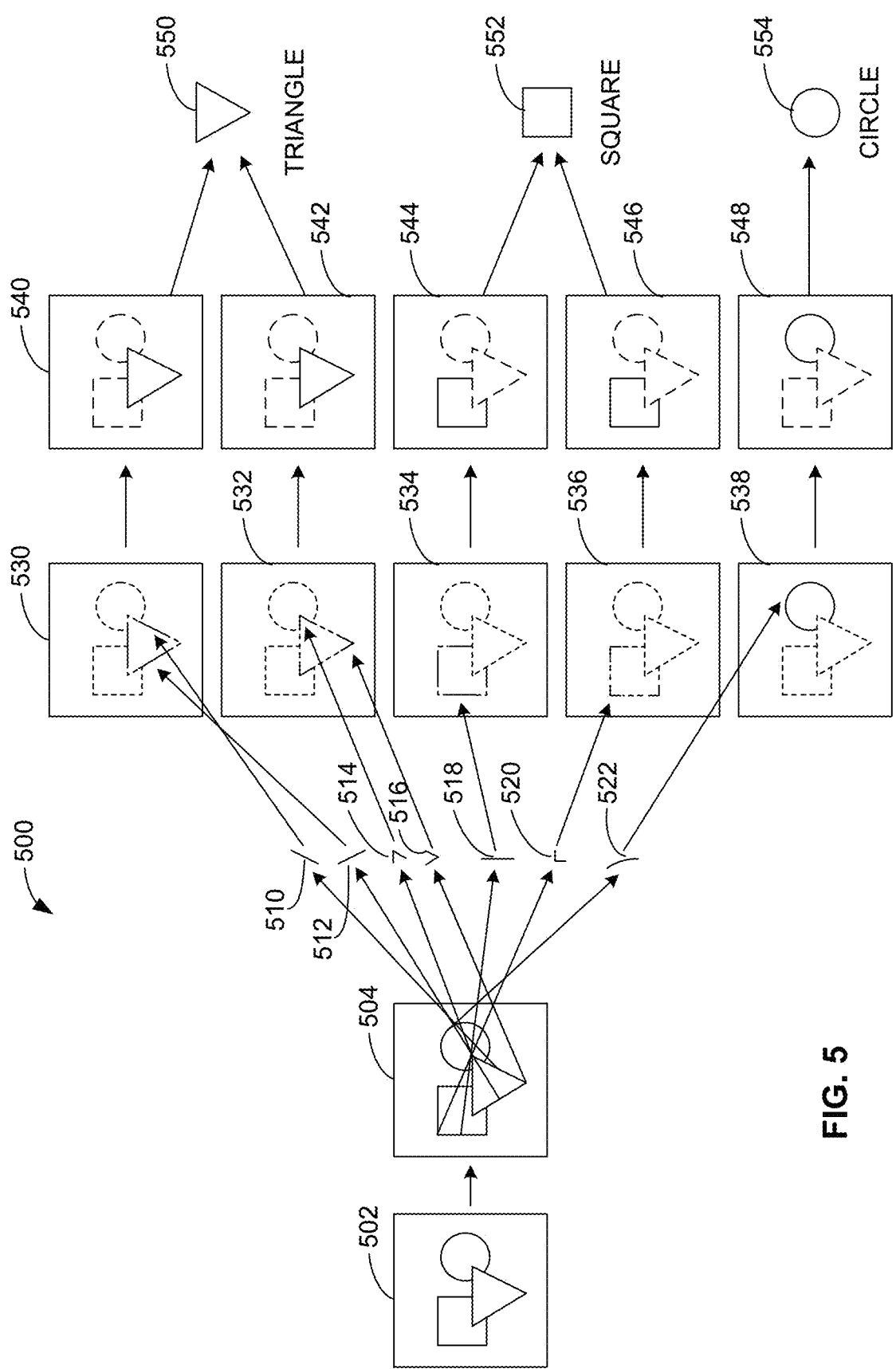
FIG. 5 is a representation of an example implementation of an image analysis convolutional neural network.

FIG. 5 is a representation of an example implementation of an image analysis convolutional neural network 500. The convolutional neural network 500 receives an input image 502 and abstracts the image in a convolution layer 504 to identify learned features 510-522. In a second convolution layer 530, the image is transformed into a plurality of images 530-538 in which the learned features 510-522 are each accentuated in a respective sub-image 530-538. The images 530-538 are further processed to focus on the features of interest 510-522 in images 540-548. The resulting images 540-548 are then processed through a pooling layer which reduces the size of the images 540-548 to isolate portions 550-554 of the images 540-548 including the features of interest 510-522. Outputs 550-554 of the convolutional neural network 500 receive values from the last non-output layer and classify the image based on the data received from the last non-output layer. In certain examples, the convolutional neural network 500 may contain many different variations of convolution layers, pooling layers, learned features, and outputs, etc.

FIG. 6A illustrates an example configuration 600 to apply a learning (e.g., machine learning, deep learning, etc.) network to process and/or otherwise evaluate an image. Machine learning can be applied to a variety of processes including image acquisition, image reconstruction, image analysis/diagnosis, etc. As shown in the example configuration 600 of FIG. 6A, raw data 610 (e.g., raw data 610 such as sonogram raw data, etc., obtained from an imaging scanner such as an x-ray, computed tomography, ultrasound, magnetic resonance, etc., scanner) is fed into a learning network 620. The learning network 620 processes the data 610 to correlate and/or otherwise combine the raw data 620 into processed data 630 (e.g., a resulting image, etc.) (e.g., a "good quality" image and/or other image providing sufficient quality for diagnosis, etc.). The learning network 620 includes nodes and connections (e.g., pathways) to associate raw data 610 with the processed data 630. The learning network 620 can be a training network that learns the connections and processes feedback to establish connections and identify patterns, for example. The learning network 620 can be a deployed network that is generated from a training network and leverages the connections and patterns established in the training network to take the input raw data 610 and generate the resulting image 630, for example.

Once the learning 620 is trained and produces good images 630 from the raw image data 610, the network 620 can continue the "self-learning" process and refine its performance as it operates. For example, there is "redundancy" in the input data (raw data) 610 and redundancy in the network 620, and the redundancy can be exploited.

If weights assigned to nodes in the learning network 620 are examined, there are likely many connections and nodes with very low weights. The low weights indicate that these connections and nodes contribute little to the overall performance of the learning network 620. Thus, these connections and nodes are redundant. Such redundancy can be evaluated to reduce redundancy in the inputs (raw data) 610. Reducing input 610 redundancy can result in savings in scanner hardware, reduced demands on components, and also reduced exposure dose to the patient, for example.

In deployment, the configuration 600 forms a package 600 including an input definition 610, a trained network 620, and an output definition 630. The package 600 can be deployed and installed with respect to another system, such as an imaging system, analysis engine, etc. An image enhancer 625 can leverage and/or otherwise work with the learning network 620 to process the raw data 610 and provide a result (e.g., processed image data and/or other processed data 630, etc.). The pathways and connections between nodes of the trained learning network 620 enable the image enhancer 625 to process the raw data 610 to form the image and/or other processed data result 630, for example.

As shown in the example of FIG. 6B, the learning network 620 can be chained and/or otherwise combined with a plurality of learning networks 621-623 to form a larger learning network. The combination of networks 620-623 can be used to further refine responses to inputs and/or allocate networks 620-623 to various aspects of a system, for example.

In some examples, in operation, "weak" connections and nodes can initially be set to zero. The learning network 620 then processes its nodes in a retaining process. In certain examples, the nodes and connections that were set to zero are not allowed to change during the retraining. Given the redundancy present in the network 620, it is highly likely that equally good images will be generated. As illustrated in FIG. 6B, after retraining, the learning network 620 becomes DLN 621. The learning network 621 is also examined to identify weak connections and nodes and set them to zero. This further retrained network is learning network 622. The example learning network 622 includes the "zeros" in learning network 621 and the new set of nodes and connections. The learning network 622 continues to repeat the processing until a good image quality is reached at a learning network 623, which is referred to as a "minimum viable net (MVN)". The learning network 623 is a MVN because if additional connections or nodes are attempted to be set to zero in learning network 623, image quality can suffer.

Once the MVN has been obtained with the learning network 623, "zero" regions (e.g., dark irregular regions in a graph) are mapped to the input 610. Each dark zone is likely to map to one or a set of parameters in the input space. For example, one of the zero regions may be linked to the number of views and number of channels in the raw data. Since redundancy in the network 623 corresponding to these parameters can be reduced, there is a highly likelihood that the input data can be reduced and generate equally good output. To reduce input data, new sets of raw data that correspond to the reduced parameters are obtained and run through the learning network 621. The network 620-623 may or may not be simplified, but one or more of the learning networks 620-623 is processed until a "minimum viable input (MVI)" of raw data input 610 is reached. At the MVI, a further reduction in the input raw data 610 may result in reduced image 630 quality. The MVI can result in reduced complexity in data acquisition, less demand on system components, reduced stress on patients (e.g., less breath-hold or contrast), and/or reduced dose to patients, for example.

By forcing some of the connections and nodes in the learning networks 620-623 to zero, the network 620-623 to build "collaterals" to compensate. In the process, insight into the topology of the learning network 620-623 is obtained. Note that network 621 and network 622, for example, have different topology since some nodes and/or connections have been forced to zero. This process of effectively removing connections and nodes from the network extends beyond "deep learning" and can be referred to as "deep-deep learning", for example.

In certain examples, input data processing and deep learning stages can be implemented as separate systems. However, as separate systems, neither module may be aware of a larger input feature evaluation loop to select input parameters of interest/importance. Since input data processing selection matters to produce high-quality outputs, feedback from deep learning systems can be used to perform input parameter selection optimization or improvement via a model. Rather than scanning over an entire set of input parameters to create raw data (e.g., which is brute force and can be expensive), a variation of active learning can be implemented. Using this variation of active learning, a starting parameter space can be determined to produce desired or "best" results in a model. Parameter values can then be randomly decreased to generate raw inputs that decrease the quality of results while still maintaining an acceptable range or threshold of quality and reducing runtime by processing inputs that have little effect on the model's quality.

Figure 7:
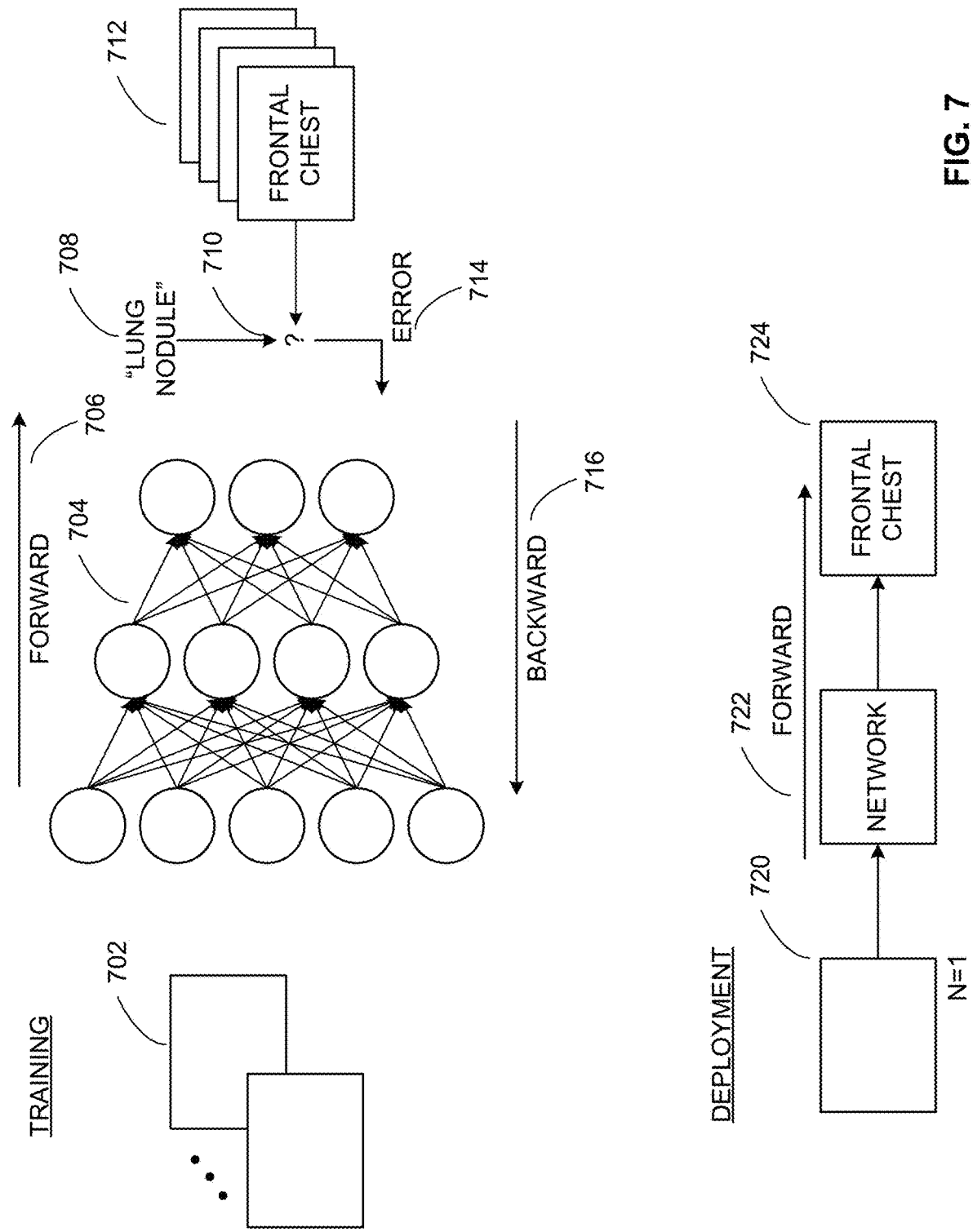
FIG. 7 illustrates example training and deployment phases of a learning network.

FIG. 7 illustrates example training and deployment phases of a learning network, such as a deep learning or other machine learning network. As shown in the example of FIG. 7, in the training phase, a set of inputs 702 is provided to a network 704 for processing. In this example, the set of inputs 702 can include facial features of an image to be identified. The network 704 processes the input 702 in a forward direction 706 to associate data elements and identify patterns. The network 704 determines that the input 702 represents a lung nodule 708. In training, the network result 708 is compared 710 to a known outcome 712. In this example, the known outcome 712 is a frontal chest (e.g., the input data set 702 represents a frontal chest identification, not a lung nodule). Since the determination 708 of the network 704 does not match 710 the known outcome 712, an error 714 is generated. The error 714 triggers an analysis of the known outcome 712 and associated data 702 in reverse along a backward pass 716 through the network 704. Thus, the training network 704 learns from forward 706 and backward 716 passes with data 702, 712 through the network 704.

Once the comparison of network output 708 to known output 712 matches 710 according to a certain criterion or threshold (e.g., matches n times, matches greater than x percent, etc.), the training network 704 can be used to generate a network for deployment with an external system. Once deployed, a single input 720 is provided to a deployed learning network 722 to generate an output 724. In this case, based on the training network 704, the deployed network 722 determines that the input 720 is an image of a frontal chest 724.

Figure 8:
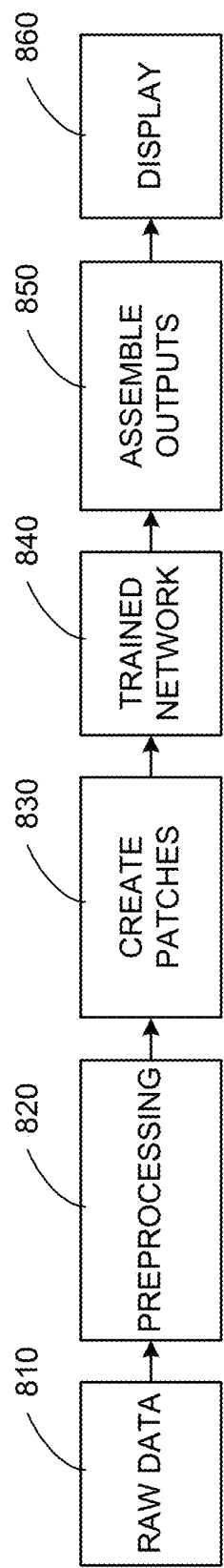
FIG. 8 illustrates an example product leveraging a trained network package to provide a deep learning product offering.

FIG. 8 illustrates an example product leveraging a trained network package to provide a deep and/or other machine learning product offering. As shown in the example of FIG. 8, an input 810 (e.g., raw data) is provided for preprocessing 820. For example, the raw input data 810 is preprocessed 820 to check format, completeness, etc. Once the data 810 has been preprocessed 820, patches are created 830 of the data. For example, patches or portions or "chunks" of data are created 830 with a certain size and format for processing. The patches are then fed into a trained network 840 for processing. Based on learned patterns, nodes, and connections, the trained network 840 determines outputs based on the input patches. The outputs are assembled 850 (e.g., combined and/or otherwise grouped together to generate a usable output, etc.). The output is then displayed 860 and/or otherwise output to a user (e.g., a human user, a clinical system, an imaging modality, a data storage (e.g., cloud storage, local storage, edge device, etc.), etc.).

Figure 9A:
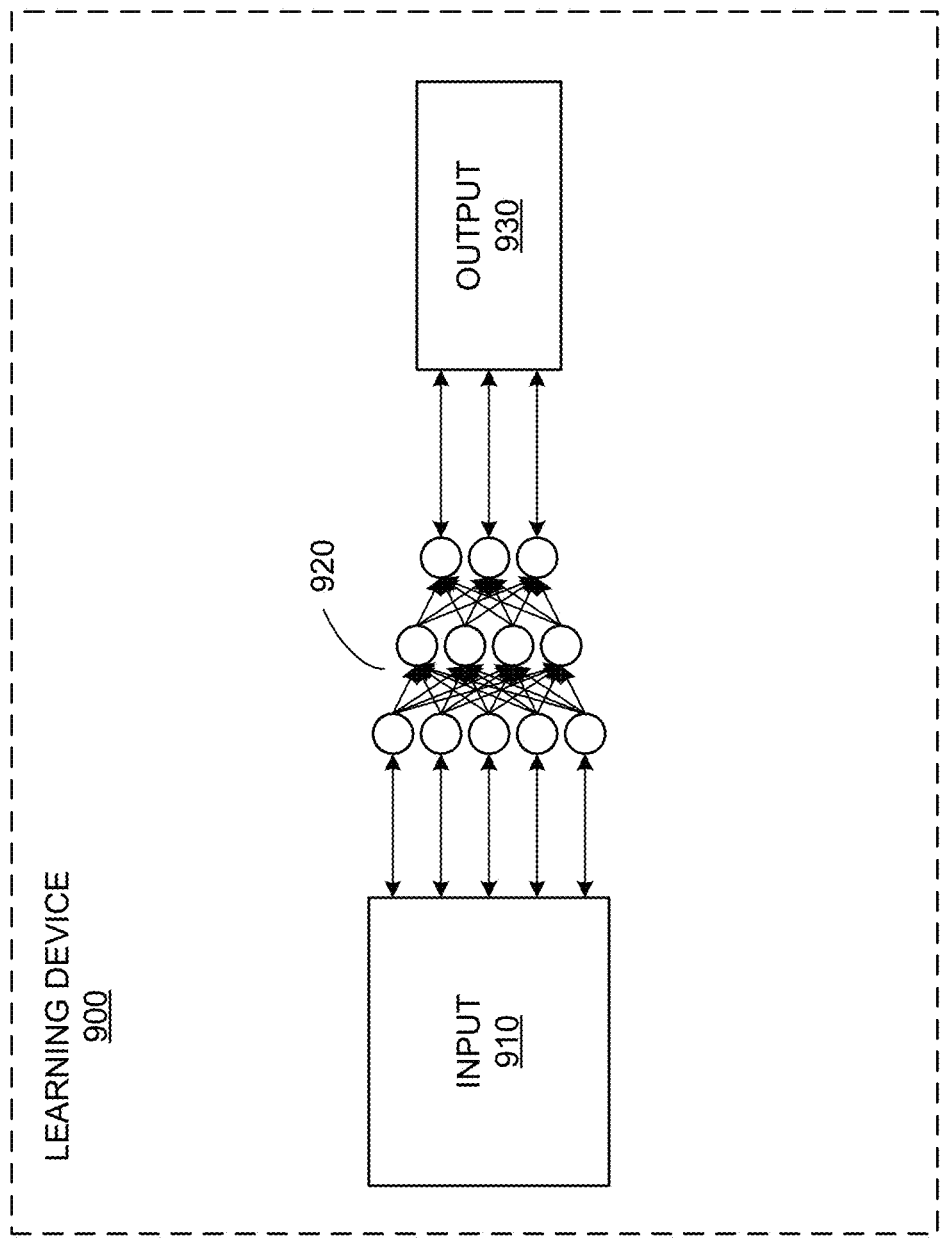
FIGS. 9A-9C illustrate various deep learning device configurations.
Figure 9B:
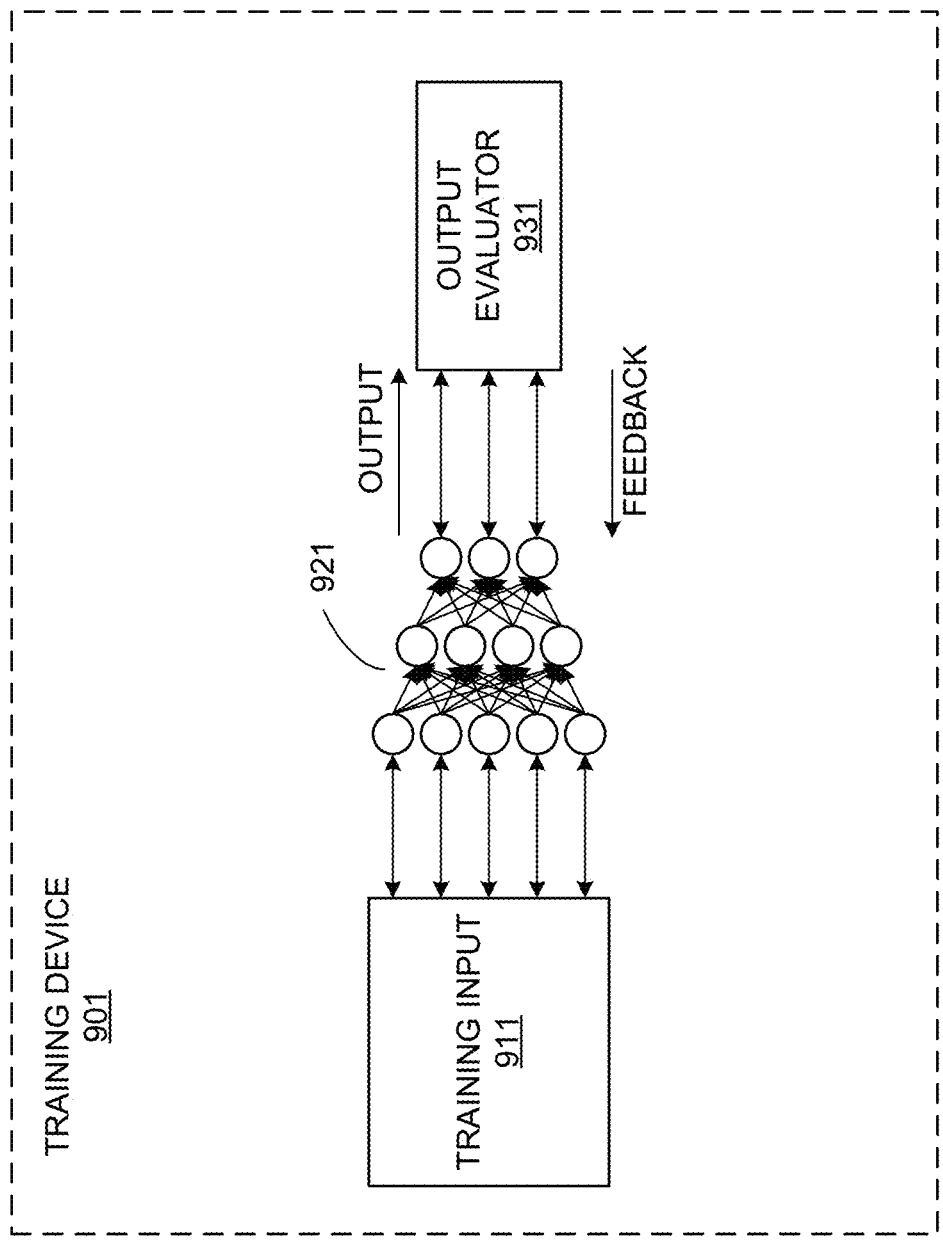
Figure 9C:
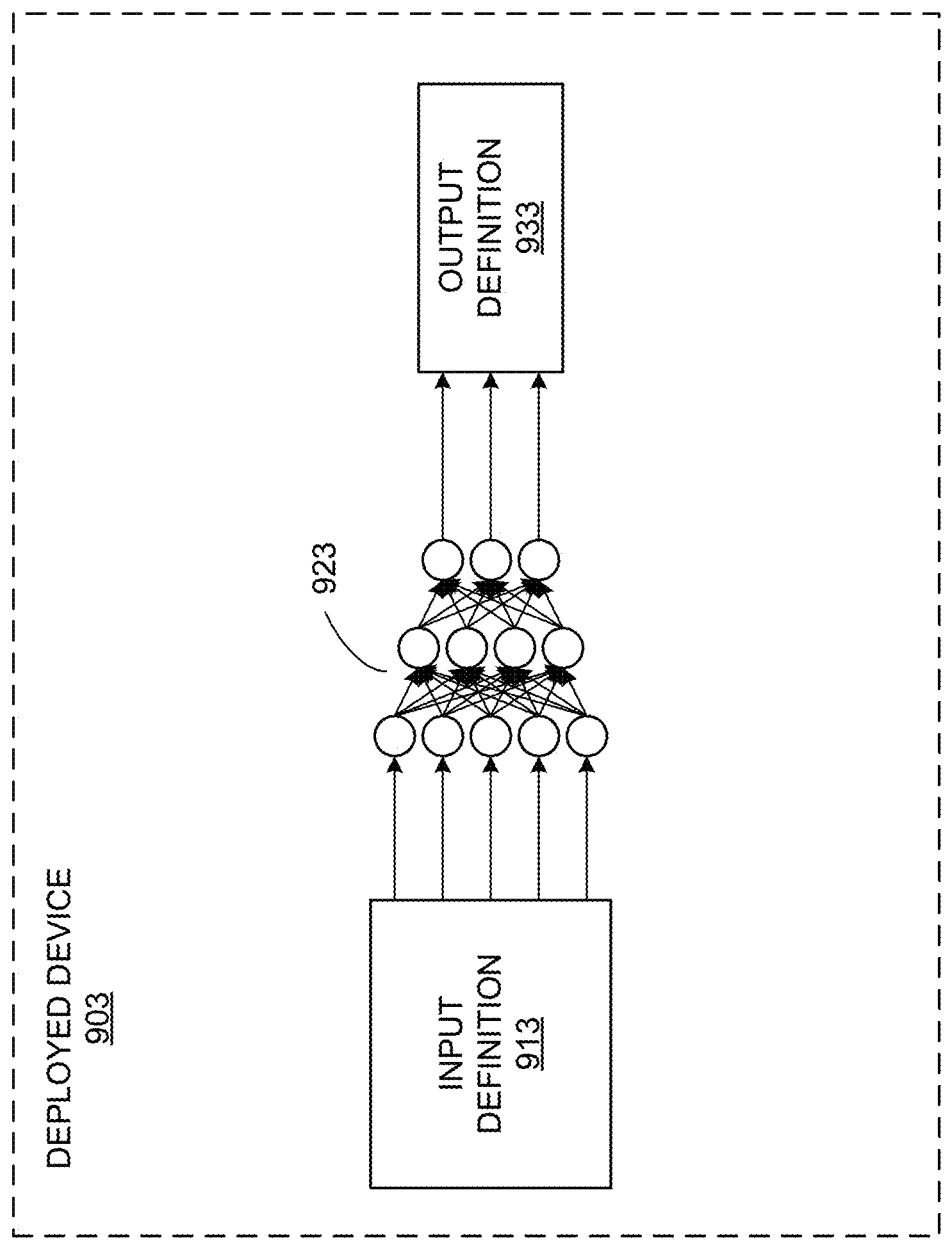

As discussed above, learning networks can be packaged as devices for training, deployment, and application to a variety of systems. FIGS. 9A-9C illustrate various learning device configurations. For example, FIG. 9A shows a general learning device 900. The example device 900 includes an input definition 910, a learning network model 920, and an output definition 930. The input definition 910 can include one or more inputs translating into one or more outputs 930 via the network 920.

FIG. 9B shows an example training device 901. That is, the training device 901 is an example of the device 900 configured as a training learning network device. In the example of FIG. 9B, a plurality of training inputs 911 are provided to a network 921 to develop connections in the network 921 and provide an output to be evaluated by an output evaluator 931. Feedback is then provided by the output evaluator 931 into the network 921 to further develop (e.g., train) the network 921. Additional input 911 can be provided to the network 921 until the output evaluator 931 determines that the network 921 is trained (e.g., the output has satisfied a known correlation of input to output according to a certain threshold, margin of error, etc.).

FIG. 9C depicts an example deployed device 903. Once the training device 901 has learned to a requisite level, the training device 901 can be deployed for use. While the training device 901 processes multiple inputs to learn, the deployed device 903 processes a single input to determine an output, for example. As shown in the example of FIG. 9C, the deployed device 903 includes an input definition 913, a trained network 923, and an output definition 933. The trained network 923 can be generated from the network 921 once the network 921 has been sufficiently trained, for example. The deployed device 903 receives a system input 913 and processes the input 913 via the network 923 to generate an output 933, which can then be used by a system with which the deployed device 903 has been associated, for example.

Example Image Processing Systems and Methods to Determine Radiological Findings

Figure 10:
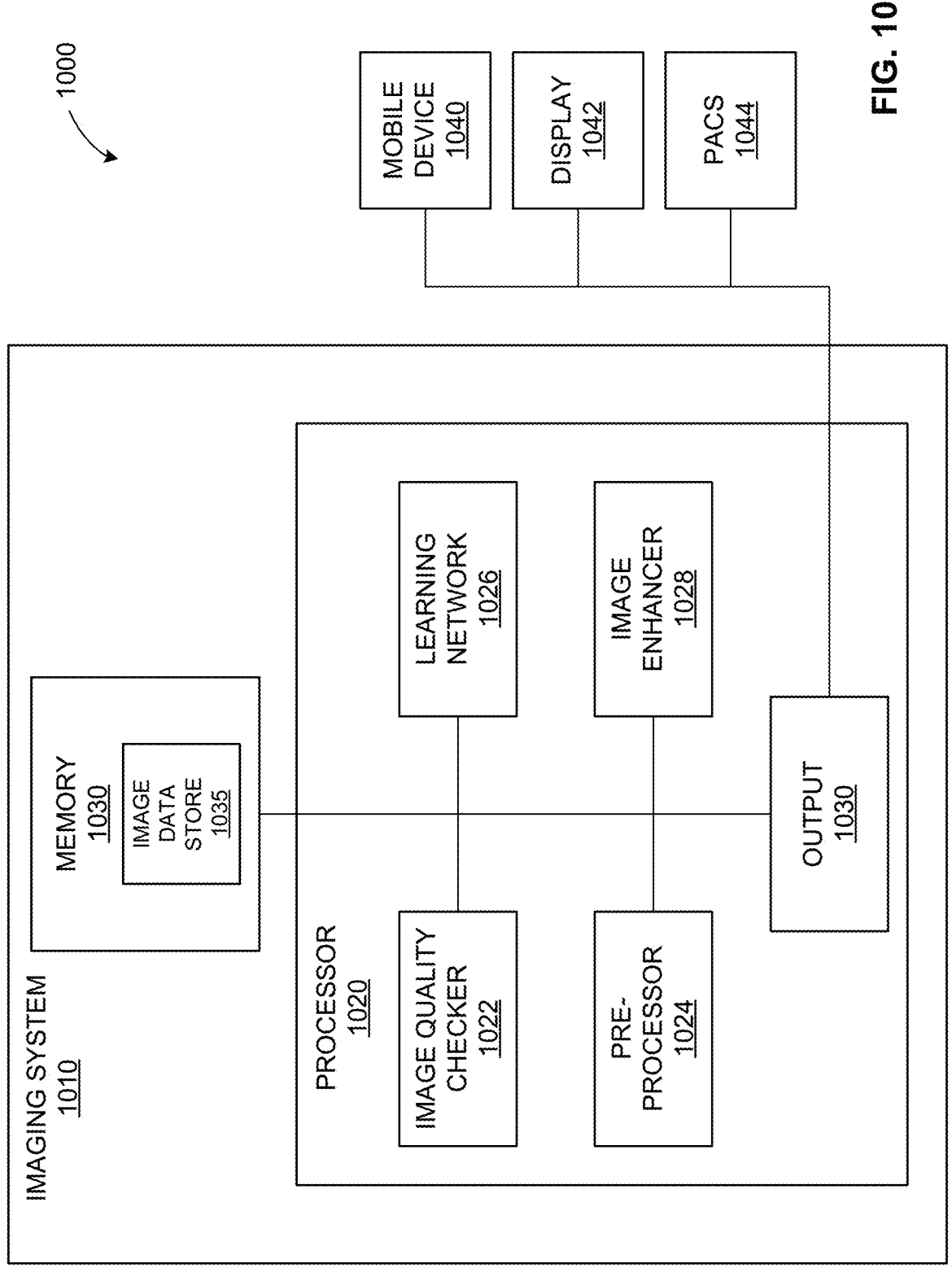
FIG. 10 illustrates an example image processing system or apparatus.

FIG. 10 illustrates an example image processing system or apparatus 1000 including an imaging system 1010 having a processor 1020 to process image data stored in a memory 1030. As shown in the example of FIG. 10, the example processor 1020 includes an image quality checker 1022, a pre-processor 1024, a learning network 1026, and an image enhancer 1028 providing information to an output 1030. Image data acquired from a patient by the imaging system 1010 can be stored in an image data store 1035 of the memory 1030, and such data can be retrieved and processed by the processor 1020.

Radiologist worklists are prioritized by putting stat images first, followed by images in order from oldest to newest, for example. By practice, most intensive care unit (ICU) chest x-rays are ordered as STAT. Since so many images are ordered as STAT, a radiologist can be unaware, among all the STAT images, which ones are really the most critical. In a large US healthcare institution, for example, a STAT x-ray order from the emergency room (ER) is typically prioritized to be read by radiologists first and is expected to be read/reported in approximately one hour. Other STAT x-ray orders, such as those acquired in the ICU, are typically prioritized next such that they may take two to four hours to be read and reported. Standard x-ray orders are typically expected to be read/reported within one radiologist shift (e.g., 6-8 hours, etc.).

Often, if there is an overnight radiologist (e.g., in larger healthcare facilities, etc.), the overnight radiologist is dedicated to reading advanced imaging exams (e.g., CT, MR, etc.), and only will read x-rays if there is a special request. Morning chest x-ray rounds commonly occur every day in the ICU, very early in the morning (e.g., 5 am, etc.). A daytime radiologist shift, however, may not start until 8 am. Then, the radiologist will sit and read through all the morning round images. If there is a critical finding, the radiologist may not find it for several hours after the image was taken.

Additionally, when a tube or line is placed within a patient, it is standard practice to take an x-ray to verify correct placement of the tube or line. Due to the delay in radiologist read/reporting, clinical care teams (e.g., nurse, intensivists, etc.) may read the chest x-ray image(s) themselves to determine if any intervention is needed (e.g., medication changes to manage fluid in the lungs, adjustment of a misplaced line/tube, or confirmation of correctly place tube so they can turn on the breathing machine or feeding tube, etc.). Depending on the clinical care team's experience, skill, or attention to detail, they may miss critical findings that compromise the patient's health by delaying diagnosis, for example. When a radiologist finds a critical finding in an x-ray, the standard practice is for them to physically call the ordering physician and discuss the finding. In some cases, the ordering physician confirms they are aware and saw the issue themselves; in other cases, it is the first time they are hearing the news and will need to quickly intervene to help the patient.

Thus, to improve image availability, system flexibility, diagnosis time, reaction time for treatment, and the like, certain examples provide an on-device/point-of-care notification of clinical finding such as to tell a clinical team at the point of care (e.g., at a patient's bedside, etc.) to review an image as the image has a high likelihood of including a critical finding. For images with critical findings, when the image is pushed to storage such as a PACS, an HL7 message can also be sent to an associated PACS/radiology information system (RIS) and/or DICOM tag, which indicates a critical finding. A hospital information system can then create/configure rules to prioritize the radiologist worklist based on this information, for example.

Turning to the example of FIG. 10, the image quality checker 1022 processes the retrieved image data to evaluate the quality of the image data according to one or more image quality measures to help ensure that the image is of sufficient quality (e.g., good quality, other expected quality, etc.) for automated (e.g., machine learning, deep learning, and/or other artificial intelligence, etc.) processing of the image data. Image data failing to pass a quality check with respect to one or more image quality measures can be rejected as of insufficient quality, with a notification generated to alert a technologist and/or other user of the quality control failure. In certain examples, artificial intelligence (AI) can be applied to analyze the image data to evaluate image quality.

By hosting an AI algorithm on the imaging device 1010, a "quality check AI" algorithm can be executed before a "critical condition AI" to help ensure that the image is of good quality/expected quality for the "critical condition AI" to perform well. The "quality check AI" can be used on the device as an assistant to the technologist ("Tech") such as when the tech performs Quality Assurance (QA)/Quality Check (QC) practices on the images they acquire. For example, after each image is acquired, the Tech may review the image to ensure proper patient positioning, collimation, exposure/technique, no patient jewelry or clothing obstructions, no artifacts, etc. If the Tech believes the image is of good quality, then the Tech will "accept" the image. However, if the image fails the QC check, the Tech can "reject" the image and "retake" the image (e.g., re-obtain the image data through a subsequent image acquisition).

Depending on the Tech's experience and skill, the Tech may have a different tolerance for accept/reject image quality. However, using AI embedded in the device 1010 allows the device 1010 processor 1020 to evaluate and notify the Tech if the image fails the "quality check AI". The image fails the quality check AI, for example, if the image is of too poor quality to reliably run through a "critical condition AI" algorithm, but simultaneously, also indicating to the Tech that perhaps the image should fail their manual/traditional QC activity as well, and that the Tech should consider a "retake". Thus, the image quality checker 1022 can provide feedback in real-time (or substantially real-time given image data processing, transmission, and/or storage/retrieval latency) such as at the patient bedside via the output 1030 of the mobile x-ray system 200, 1010 indicating/recommending that an image should be re-acquired, for example.

Thus, rather than relying on a Tech's manual assessment, the quality checker 1022 can leverage AI and/or other processing to analyze image anatomy, orientation/position, sufficient contrast, appropriate dose, too much noise/artifacts, etc., to evaluate image quality and sufficiency to enable further automated analysis.

If image quality is sufficient and/or otherwise appropriate (e.g., correct view/position, correct anatomy, acceptable contrast and/or noise level, etc.) for analysis, then the pre-processor 1024 processes the image data and prepares the image data for clinical analysis. For example, the image data can be conditioned for processing by machine learning, such as a deep learning network, etc., to identify one or more features of interest in the image data. The pre-processor 1024 can apply techniques such as image segmentation to identify and divide different regions or areas in the image, for example. The pre-processor 1024 can apply techniques such as cropping to select a certain region of interest in the image for further processing and analysis, for example. The pre-processor 1024 can apply techniques such as downsampling to scale or reduce image data size for further processing (e.g., by presenting the learning network 1026 with fewer samples representing the image data, etc.), for example.

The pre-processed image data is provided to the learning network 1026 for processing of the image data to identify one or more clinical/critical findings. As discussed above, the learning network 1026, such as a deep learning network, other CNN, and/or other machine learning network, etc., receives the pre-processed image data at its input nodes and evaluates the image data according to the nodes and connective pathways of the learning network 1026 to correlate features identified in the pre-processed image data with critical and/or other clinical findings. Based on image intensity values, reference coordinate position, proximity, and/or other characteristics, items determined in the image data can be correlated with likely critical and/or other clinical findings such as a severe pneumothorax, tube within the right mainstem, free air in the bowel, etc.

For example, a large, highly curated set of X-Ray images can be used to train a deep convolution network (e.g., the example network of FIGS. 3-5, etc.) including several layers in an offline compute-intensive environment. The network is trained to output classification labels depicting a detected pathology and are able to extract features that can localize and bound regions interest to the detected pathology. The specialized network is developed and trained to output quantification metrics such as fluid density, opacity and volumetric measurements, etc. As shown in the example of FIGS. 6A-9C, trained model(s) are deployed onto an X-Ray device (e.g., the imaging device 10, 200, 1010, etc.) which is either mobile or installed in a fixed X-Ray room. The processor 1020 leverages the trained, deployed model(s) to infer properties, features, and/or other aspects of the image data by inputting the X-Ray image into the trained network model(s). The deployed model(s) help check quality and suitability of the image for inference via the image quality checker 1022 and infer findings via the learning network 1026, for example. The images can be pre-processed in real time based on acquisition conditions that generated the image to improve accuracy and efficacy of the inference process. In certain examples, the learning network(s) 1026 are trained, updated, and redeployed continuously and/or periodically upon acquisition of additional curated data. As a result, more accurate and feature enhanced networks are deployed on the imaging device 1010.

In certain examples, a probability and/or confidence indicator or score can be associated with the indication of critical and/or other clinical finding(s), a confidence associated with the finding, a location of the finding, a severity of the finding, a size of the finding, and/or an appearance of the finding in conjunction with another finding or in the absence of another finding, etc. For example, a strength of correlation or connection in the learning network 1026 can translate into a percentage or numerical score indicating a probability of correct detection/diagnosis of the finding in the image data, a confidence in the identification of the finding, etc.

The image data and associated finding(s) can be provided via the output 1030 to be displayed, reported, logged, and/or otherwise used in a notification or alert to a healthcare practitioner such as a Tech, nurse, intensivist, trauma surgeon, etc., to act quickly on the critical and/or other clinical finding. In some examples, the probability and/or confidence score, and/or a criticality index/score associated with the type of finding, size of finding, location of finding, etc., can be used to determine a severity, degree, and/or other escalation of the alert/notification to the healthcare provider. For example, certain detected conditions result in a text-based alert to a provider to prompt the provider for closer review. Other, more serious conditions result in an audible and/or visual alert to one or more providers for more immediate action. Alert(s) and/or other notification(s) can escalate in proportion to an immediacy and/or other severity of a probable detected condition, for example.

Image data and associated finding(s) can be provided to image enhancer 1028 for image post-processing to enhance the image data. For example, the image enhancer 1028 can process the image data based on the finding(s) to accentuate the finding(s) in a resulting image. Thus, when the enhanced image data is provided to the output 1030 for display (e.g., via one or more devices such as a mobile device 1040, display 1042, PACS and/or other information system 1044, etc.), the finding(s) are emphasized, highlighted, noted, and/or otherwise enhanced in the resulting displayed image, for example.

By running AI on the imaging device 1010, AI findings can be leveraged to conduct enhanced image processing. For example, if the AI detects tubes/lines present in the image data, then the device software can process the image using an image processing technique best for viewing tubes/lines. For example, tubes and/or other lines (e.g., catheter, feeding tube, nasogastric (NG) tube, endotracheal (ET) tube, chest tube, pacemaker leads, etc.) can be emphasized or enhanced in the image data through an image processing algorithm that decomposes the image data into a set of spatial frequency bands. Non-linear functions can be applied to the frequency bands to enhance contrast and reduce noise in each band. Spatial frequencies including tubes and lines are enhanced while spatial frequencies including noise are suppressed. As a result, the tubes and lines are more pronounced in a resulting image. Similarly, a pneumothorax (e.g., an abnormal collection of air in pleural space between a lung and the chest), fracture, other foreign object, etc., representing a finding can be emphasized and/or otherwise enhanced in a resulting image, for example.

The enhanced image data and associated finding(s) can be output for display, storage, referral, further processing, provision to a computer-aided diagnosis (CAD) system, etc., via the output 1030. The output 1030 can provide information to a plurality of connected devices 1040-1044 for review, storage, relay, and/or further action, for example.

While example implementations are illustrated in conjunction with FIGS. 1-10, elements, processes and/or devices illustrated in conjunction with FIGS. 1-10 can be combined, divided, re-arranged, omitted, eliminated and/or implemented in any other way. Further, components disclosed and described herein can be implemented by hardware, machine readable instructions, software, firmware and/or any combination of hardware, machine readable instructions, software and/or firmware. Thus, for example, components disclosed and described herein can be implemented by analog and/or digital circuit(s), logic circuit(s), programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the components is/are hereby expressly defined to include a tangible computer readable storage device or storage disk such as a memory, a digital versatile disk (DVD), a compact disk (CD), a Blu-ray disk, etc. storing the software and/or firmware.

Figure 11:
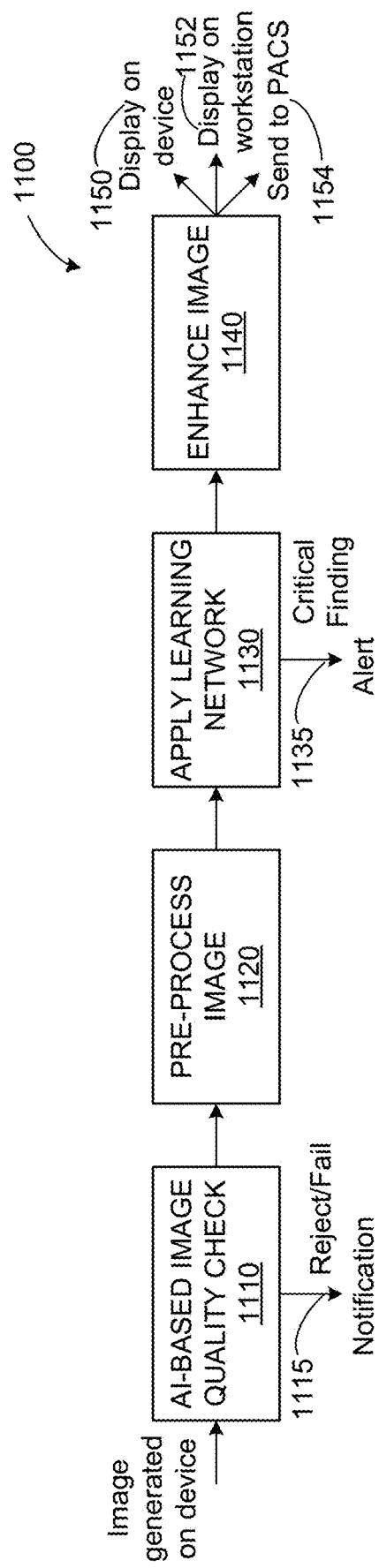
FIGS. 11-12 illustrate flow diagrams for example methods of automated processing and image analysis to present findings at the point of care in accordance with the systems and/or apparatus of FIGS. 1-10.
Figure 12:
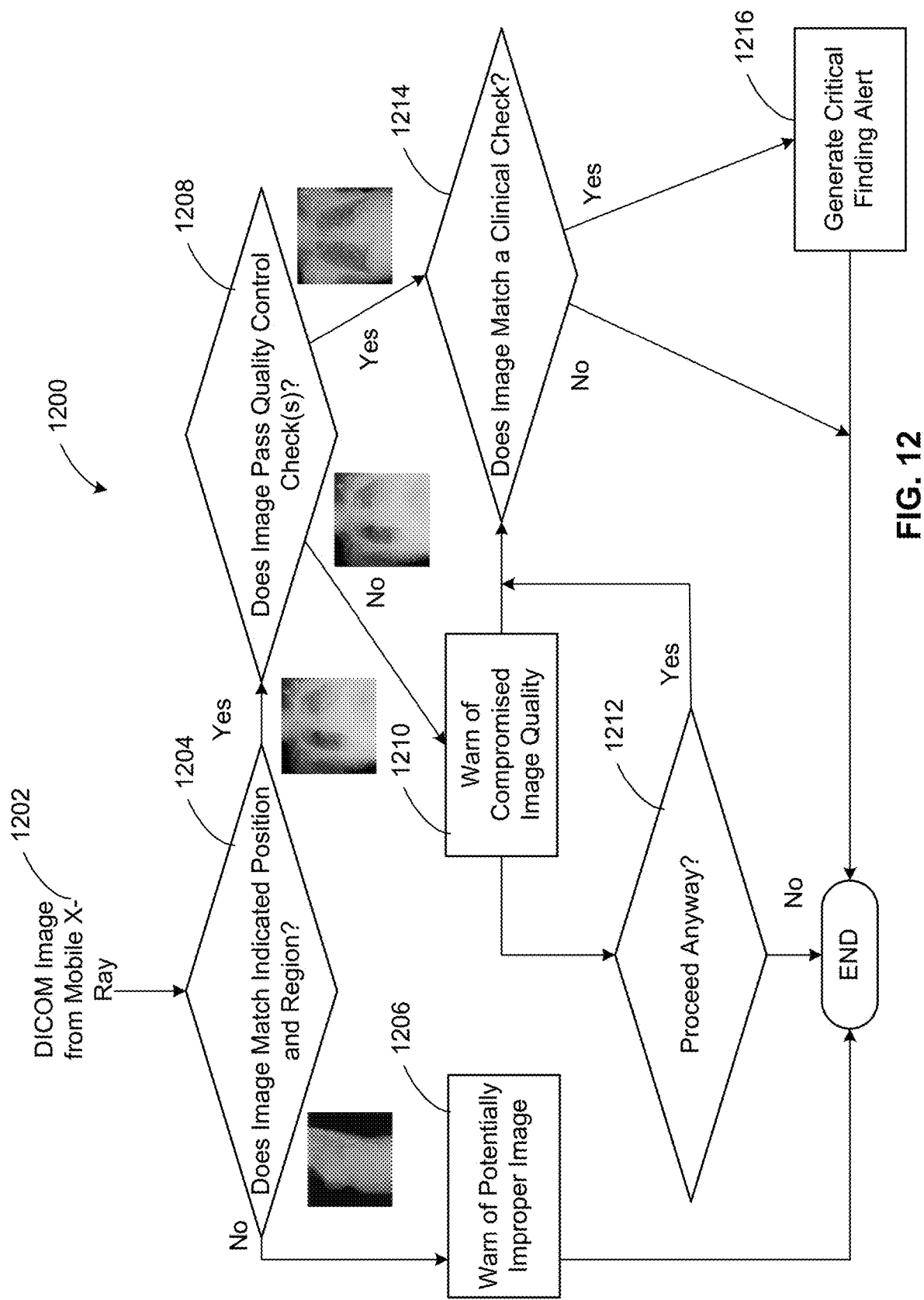

Flowcharts representative of example machine readable instructions for implementing components disclosed and described herein are shown in conjunction with at least FIGS. 11-12. In the examples, the machine readable instructions include a program for execution by a processor such as the processor 1312 shown in the example processor platform 1300 discussed below in connection with FIG. 13. The program may be embodied in machine readable instructions stored on a tangible computer readable storage medium such as a CD-ROM, a floppy disk, a hard drive, a digital versatile disk (DVD), a Blu-ray disk, or a memory associated with the processor 1312, but the entire program and/or parts thereof could alternatively be executed by a device other than the processor 1312 and/or embodied in firmware or dedicated hardware. Further, although the example program is described with reference to the flowcharts illustrated in conjunction with at least FIGS. 11-12, many other methods of implementing the components disclosed and described herein may alternatively be used. For example, the order of execution of the blocks may be changed, and/or some of the blocks described may be changed, eliminated, or combined. Although the flowcharts of at least FIGS. 11-12 depict example operations in an illustrated order, these operations are not exhaustive and are not limited to the illustrated order. In addition, various changes and modifications may be made by one skilled in the art within the spirit and scope of the disclosure. For example, blocks illustrated in the flowchart may be performed in an alternative order or may be performed in parallel.

As mentioned above, the example processes of at least FIGS. 11-12 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of at least FIGS. 11-12 can be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended. In addition, the term "including" is open-ended in the same manner as the term "comprising" is open-ended.

As shown in the example method 1100 depicted in FIG. 11, acquired image data can be analyzed by the imaging device 1010 at the location of image acquisition (e.g., patent bedside, imaging room, etc.) to evaluate image quality and identify likely critical and/or other clinical findings to trigger further image and patient review and action. At block 1110, acquired image data acquired by the device 1010 is processed by the device 1010 to evaluate the quality of the image data to help ensure that the image is of sufficient quality (e.g., good quality, other expected quality, etc.) for automated (e.g., machine learning, deep learning, and/or other artificial intelligence, etc.) processing of the image data. Image data failing to pass a quality check can be rejected as of insufficient quality, with a notification generated to alert a technologist and/or other user of the quality control failure. In certain examples, artificial intelligence (AI) can be applied by the image quality checker 1022 to analyze the image data to evaluate image quality.

By hosting an AI algorithm on the imaging device 1010, a "quality check AI" algorithm can be executed before a "critical condition AI" to help ensure that the image is of good quality/expected quality for the "critical condition AI" to perform well. The "quality check AI" can be used on the device as an assistant to the technologist ("Tech") such as when the tech performs Quality Assurance (QA)/Quality Check (QC) practices on the images they acquire. Using AI embedded in the device 1010 allows the device 1010 processor 1020 to evaluate and notify 1115 the Tech if the image fails the "quality check AI". The image fails the quality check AI, for example, if the image is of too poor quality to reliably run through a "critical condition AI" algorithm, but simultaneously, also indicating to the Tech that perhaps the image should fail their manual/traditional QC activity as well, and that the Tech should consider a "retake". Thus, the image quality checker 1022 can provide feedback in real-time (or substantially real-time given image data processing, transmission, and/or storage/retrieval latency) such as at the patient bedside via the output 1030 of the mobile x-ray system 200, 1010 indicating/recommending via a notification 1115 that an image should be re-acquired, for example. For example, the notification 1115 can be provided via an overlay on the mobile device 1040, display 1042, etc., to show localization (e.g., via a heatmap, etc.) of the AI finding and/or associated information.

Thus, rather than relying on a Tech's manual assessment, the quality checker 1022 can leverage AI and/or other processing to analyze image anatomy, orientation/position, sufficient contrast, appropriate dose, too much noise/artifacts, etc., to evaluate image quality and sufficiency to enable further automated analysis.

If image quality is sufficient and/or otherwise appropriate (e.g., correct view/position, correct anatomy, acceptable patient positioning, contrast and/or noise level, etc.) for analysis, then, at block 1120, the image data is pre-processed to prepare the image data for clinical analysis. For example, the image data can be conditioned for processing by machine learning, such as a deep learning network, etc., to identify one or more features of interest in the image data. The pre-processor 1024 can apply techniques such as image segmentation to identify and divide different regions or areas in the image, for example. The pre-processor 1024 can apply techniques such as cropping to select a certain region of interest in the image for further processing and analysis, for example. The pre-processor 1024 can apply techniques such as down-sampling, anatomical segmentation, normalizing with mean and/or standard deviation of training population, contrast enhancement, etc., to scale or reduce image data size for further processing (e.g., by presenting the learning network 1026 with fewer samples representing the image data, etc.), for example.

At block 1130, the pre-processed image data is provided to the learning network 1026 for processing of the image data to identify one or more clinical/critical findings. As discussed above, the learning network 1026, such as a deep learning network, other CNN and/or other machine learning network, etc., receives the pre-processed image data at its input nodes and evaluates the image data according to the nodes and connective pathways of the learning network 1026 to correlate features identified in the pre-processed image data with critical and/or other clinical findings. Based on image intensity values, reference coordinate position, proximity, and/or other characteristics, items determined in the image data can be correlated with likely critical and/or other clinical findings such as a severe pneumothorax, tube within the right mainstem, free air in the bowel, etc.

For example, a large, highly curated set of X-Ray images can be used to train a deep convolution network (e.g., the example network of FIGS. 3-5, etc.) including several layers in an offline compute-intensive environment. The network is trained to output classification labels depicting a detected pathology and are able to extract features that can localize and bound regions interest to the detected pathology. The specialized network is developed and trained to output quantification metrics such as fluid density, opacity and volumetric measurements, etc. As shown in the example of FIGS. 6A-9C, trained model(s) are deployed onto an X-Ray device (e.g., the imaging device 10, 200, 1010, etc.) which is either mobile or installed in a fixed X-Ray room. The processor 1020 leverages the trained, deployed model(s) to infer properties, features, and/or other aspects of the image data by inputting the X-Ray image into the trained network model(s). The deployed model(s) help check quality and suitability of the image for inference via the image quality checker 1022 and infer findings via the learning network 1026, for example. The images can be pre-processed in real time based on acquisition conditions that generated the image to improve accuracy and efficacy of the inference process. In certain examples, the learning network(s) 1026 are trained, updated, and redeployed continuously and/or periodically upon acquisition of additional curated data. As a result, more accurate and feature enhanced networks are deployed on the imaging device 1010.

In certain examples, a probability and/or confidence indicator or score can be associated with the indication of critical and/or other clinical finding(s), as well as a size of the finding, location of the finding, severity of the finding, etc. For example, a strength of correlation or connection in the learning network 1026 can translate into a percentage or numerical score indicating a probability of correct detection/diagnosis of the finding in the image data, a confidence in the identification of the finding, etc.

The image data and associated finding(s) can be provided via the output 1030 to be displayed, reported, logged, and/or otherwise used in a notification or alert 1135 to a healthcare practitioner such as a Tech, nurse, intensivist, trauma surgeon, and/or clinical system, etc., to act quickly on the critical and/or other clinical finding. In some examples, the probability and/or confidence score, and/or a criticality index/score associated with the type of finding, can be used to determine a severity, degree, and/or other escalation of the alert/notification to the healthcare provider. For example, certain detected conditions result in a text-based alert to a provider to prompt the provider for closer review. Other, more serious conditions result in an audible and/or visual alert to one or more providers for more immediate action. Alert(s) and/or other notification(s) can escalate in proportion to an immediacy and/or other severity of a probable detected condition, for example.

At block 1140, image data is enhanced based on associated finding(s) identified by the learning network 1026. For example, the image enhancer 1028 can process the image data based on the finding(s) to accentuate the finding(s) in a resulting image. Thus, when the enhanced image data is provided to the output 1030 for display (e.g., via one or more devices such as a mobile device 1040, display 1042, PACS and/or other information system 1044, etc.), the finding(s) are emphasized, highlighted, noted, and/or otherwise enhanced in the resulting displayed image, for example.

By running AI on the imaging device 1010, AI findings can be leveraged to conduct enhanced image processing. For example, if the AI detects tubes/lines present in the image data, then the device software can process the image using an image processing technique best for viewing tubes/lines.

The enhanced image data and associated finding(s) can be output for display, storage, referral, further processing, provision to a computer-aided diagnosis (CAD) system, etc., via the output 1030. The output 1030 can provide information to a plurality of connected devices 1040-1044 for review, storage, relay, and/or further action, for example. As shown in the example of FIG. 11, enhanced image data and associated finding(s) can be output for display on a device 1150 (e.g., a handheld or mobile device, etc.), displayed on a workstation 1152 (e.g., an information system, a display associated with the imaging device 1010, etc.), and/or sent to a clinical information system such as a PACS, RIS, enterprise archive, etc., for storage and/or further processing 1154.

FIG. 12 illustrates a flow diagram for example implementation of checking image quality (1110) and applying artificial intelligence (1130) to image data to determine critical and/or other clinical findings in the image data.

Portable, real-time, at point of patient care, at point of image acquisition, dynamic determination and prompting for further action, integrated into imaging device. At 1202, image data, such as DICOM image data, is provided from a mobile x-ray imaging device (e.g., the device 200 and/or 1010, etc.). At 1204, metadata associated with the image data (e.g., DICOM header information, other associated metadata, etc.) is analyzed to determine whether the image data matches a position and region indicated by the metadata. For example, if the DICOM metadata indicates that the image is a frontal (e.g., anteroposterior (AP) or posteroanterior (PA)) chest image, then an analysis of the image data should confirm that position (e.g., location and orientation, etc.). If the image does not match its indicated position and region, then, at 1206, a notification, alert, and/or warning is generated indicating that the image is potentially improper. The warning can be an audible, visual, and/or system alert or other notification, for example, and can prompt a user for further action (e.g., re-acquire the image data, etc.), trigger a system for further action, log the potential error, etc.

If the image data appears to match its prescribed position and region, then, at 1208, the image data is analyzed to determine whether the image passes image quality control check(s). For example, the image data is analyzed to determine whether the associated image has good patient positioning (e.g., the patient is positioned such that an anatomy or region of interested is centered in the image, etc.). Other quality control checks can include an evaluation of sufficient contrast, an analysis of a level of noise or artifact in the image, an examination of appropriate/sufficient dosage for image clarity, etc.

If the image fails a quality control check, then, at 1210, a warning of compromised image quality is generated. For example, a user, other system, etc., can receive an alert and/or other notification (e.g., a visual and/or audible alert on screen, via message, log notation, trigger, etc.) that the image quality may not be sufficient and/or may present issues in evaluating the image data to determine clinical finding(s). At 1212, settings and/or other input is evaluated to determine whether to proceed with further image processing. For example, user input in response to the notification can indicate whether or not to proceed anyway, and/or a configuration setting, etc., can specify a default instruction or threshold regarding whether or not to proceed with further image analysis despite image quality concerns. If the instruction is not to proceed, then the process 1200 ends.

If analysis is to proceed (e.g., because the image passes quality check(s) and/or an instruction indicates to proceed despite image quality concerns, etc.), then, at 1214, the image data is evaluated with respect to a clinical check. For example, a deep learning network, machine learning, and/or other AI is applied to analyze the image data to detect the presence of a critical and/or other clinical finding. For example, image data can be processed by the learning network 1026 to identify a severe pneumothorax and/or other condition (e.g., tube within the right mainstem, free air in the bowel, fracture, tumor, lesion, other foreign object, etc.) in the image data. If no finding is determined, then the process 1200 ends.

If, however, a finding is determined, then, at 1216, a finding alert and/or other notification is generated. For example, a critical finding alert is generated based on the identification of a pneumothorax, incorrect position of an ET tube, position of tube in right main stem, etc. The alert can be generated in proportion to and/or other correlation with a severity/urgency of the clinical finding, confidence in the finding, type of finding, location of the finding, and/or appearance of the finding in conjunction with another finding or in absence of another finding, for example. For example, a critical finding can be alerted more urgently to a healthcare practitioner and/or other user than a less-critical clinical finding. On-screen alert(s) can be 13-displayed, HL7 messages can be provided to the RIS, etc. In certain examples, image data can be re-processed such as by the image enhancer 1028 to more optimally display the finding(s) to a user.

FIGS. 13-20 illustrate example displays to provide output and facilitate interaction including on-screen alerts, indicators, notifications, etc., in accordance with the apparatus, systems, and methods described above in connection with FIGS. 1-12. The example displays can be provided via the imaging devices 10, 200, 1010, and/or a separate handheld or mobile computing device, workstation, etc.

Figure 13:
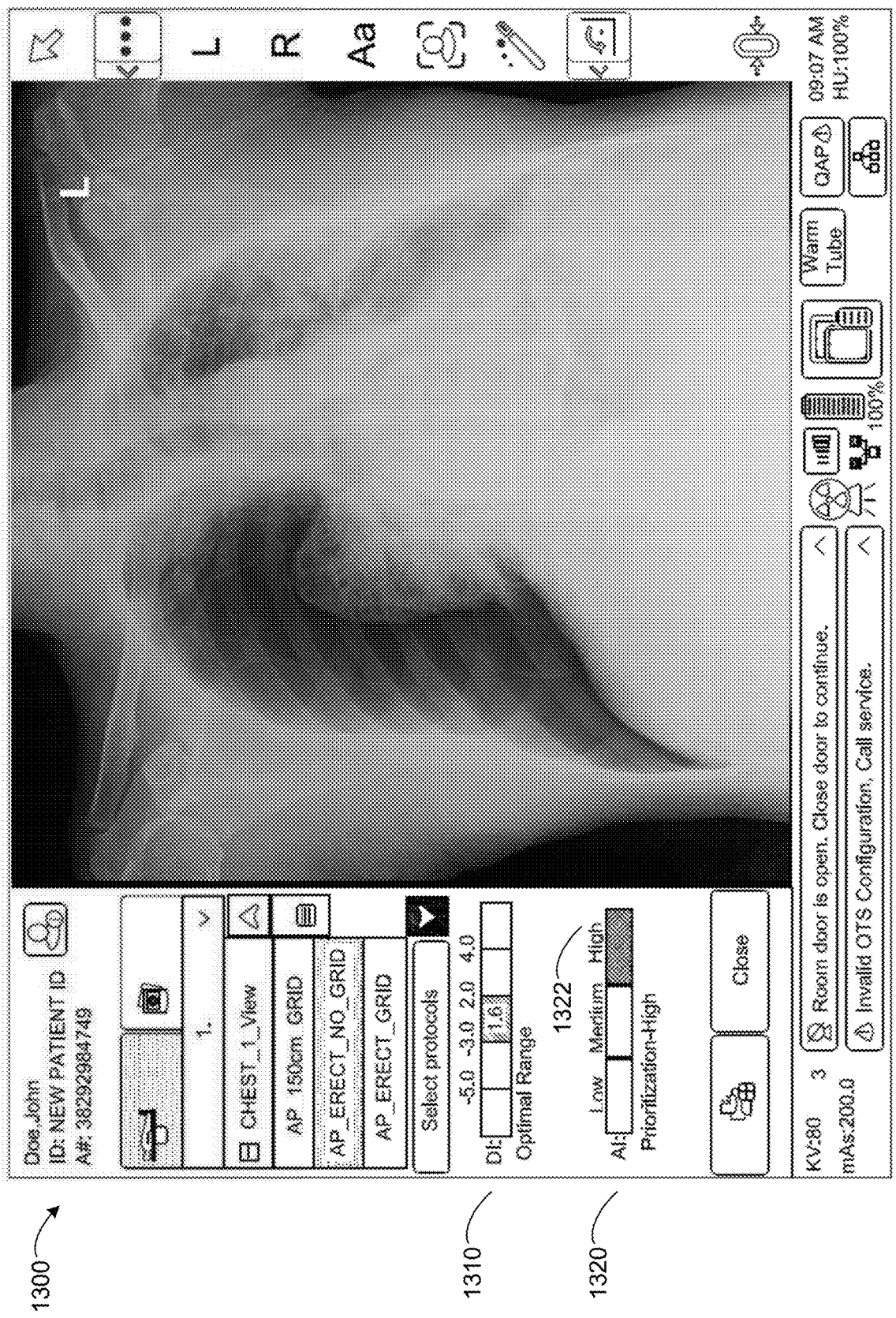
Figure 14:
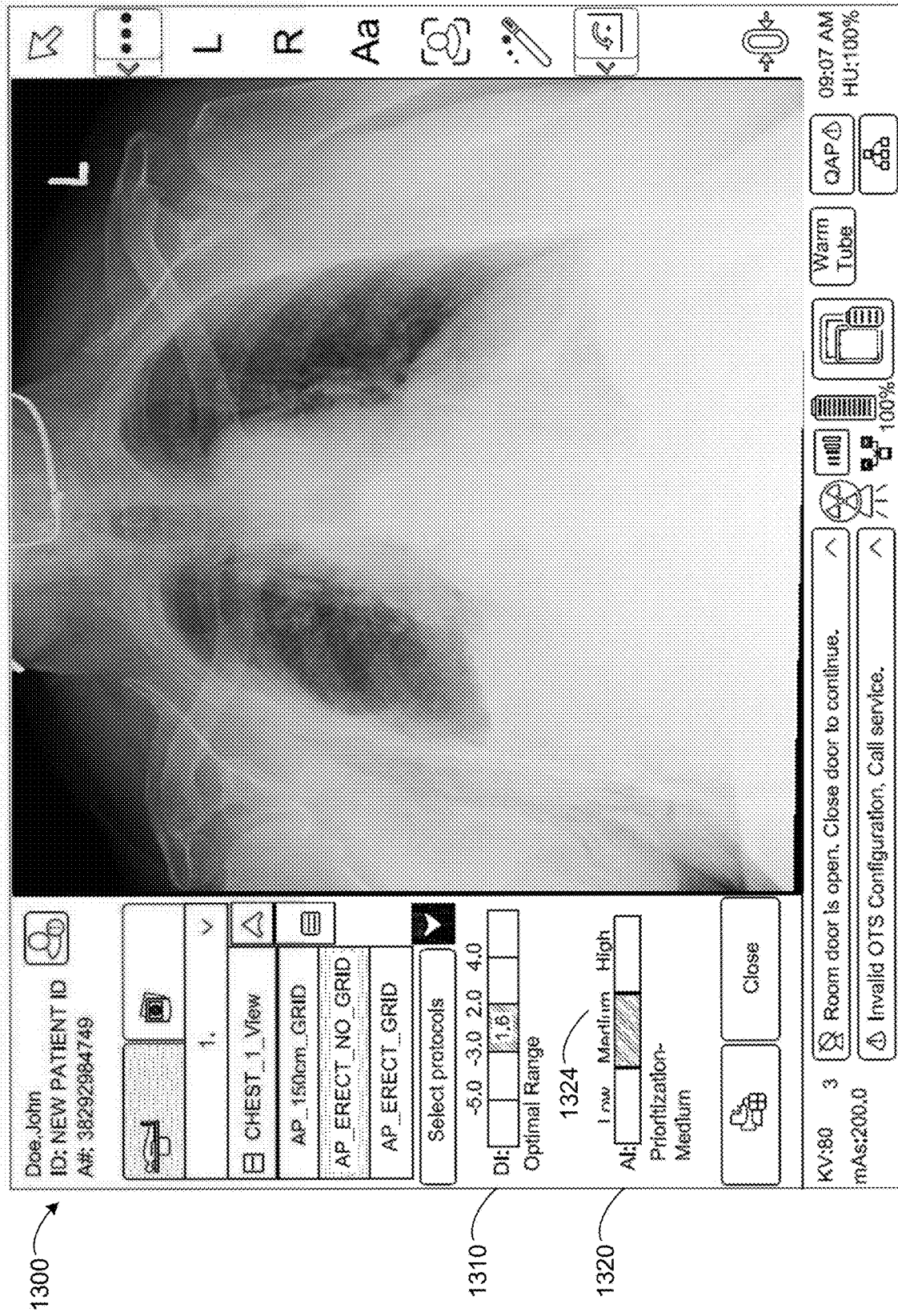
Figure 15:
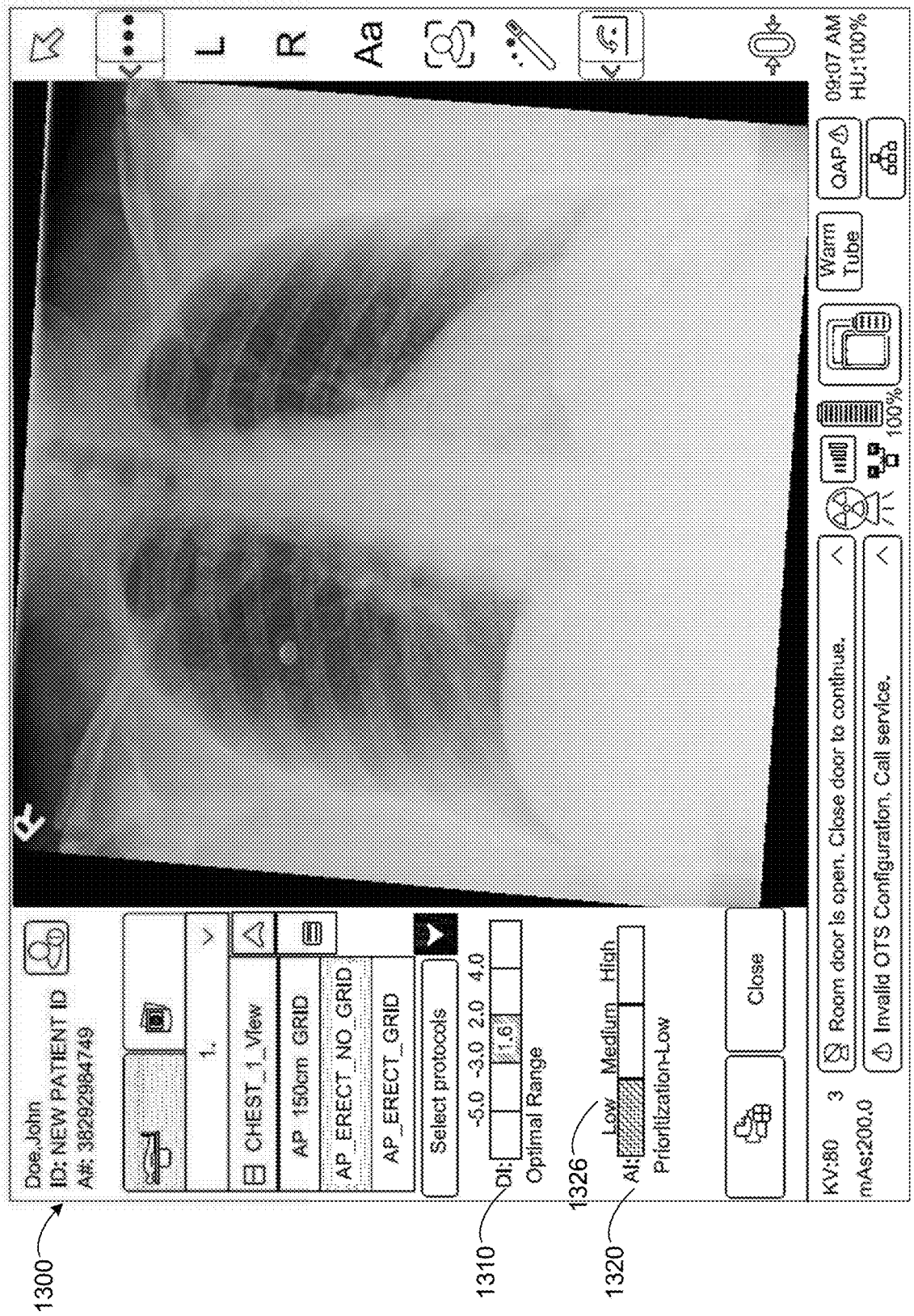

FIG. 13 shows an example graphical user interface (GUI) 1300 including a deviation index (DI) 1310 (e.g., an indication of correct image acquisition technique with 0.0 being a perfect exposure) and an indication of priority 1320 (e.g., from processing by the system 1000 including AI). As shown in the example of FIG. 13, the priority indication 1320 is high 1322. FIG. 14 illustrates the example GUI 1300 with a priority indication 1320 of medium 1324. FIG. 15 illustrates the example GUI 1300 with a priority indication 1310 of low 1326.

Figure 16:
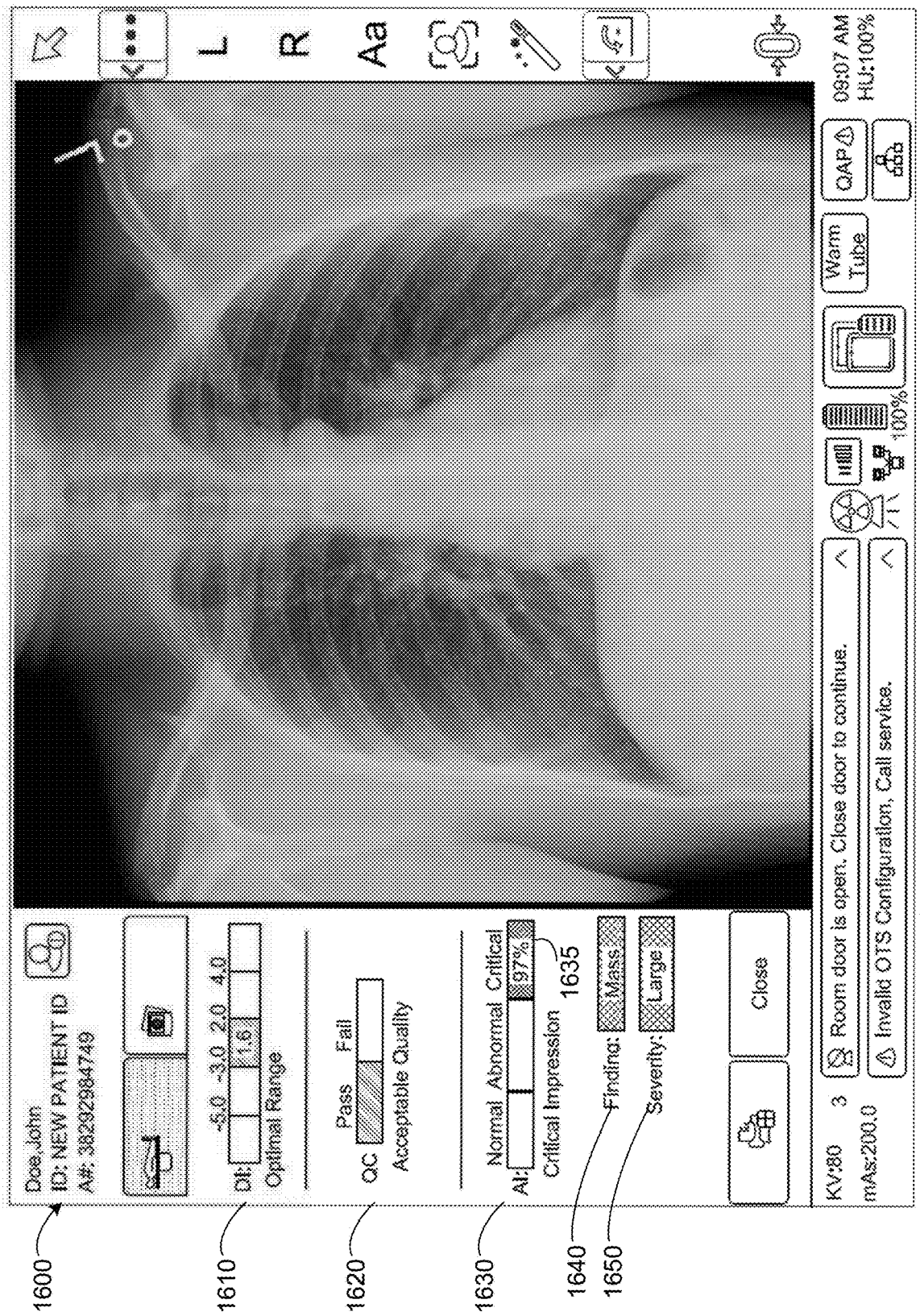

FIG. 16 illustrates an example GUI 1600 including a DI 1610, a quality control indicator 1620 (e.g., pass or fail for acceptable quality, etc.), a criticality index 1630 (e.g., normal, abnormal, critical, etc.), a criticality value 1635 associated with the criticality index 1630, an indication of finding 1640 (e.g., mass, fracture, pneumothorax, etc.), and an indication of size or severity 1650 (e.g., small, medium, large, etc.). Thus, a user can interact with the example GUI 1600 and evaluate the DI 1610, quality indication 1620, criticality range 1630 and value 1635 for clinical impression, type of finding 1640, and severity of finding 1650.

Figure 17:
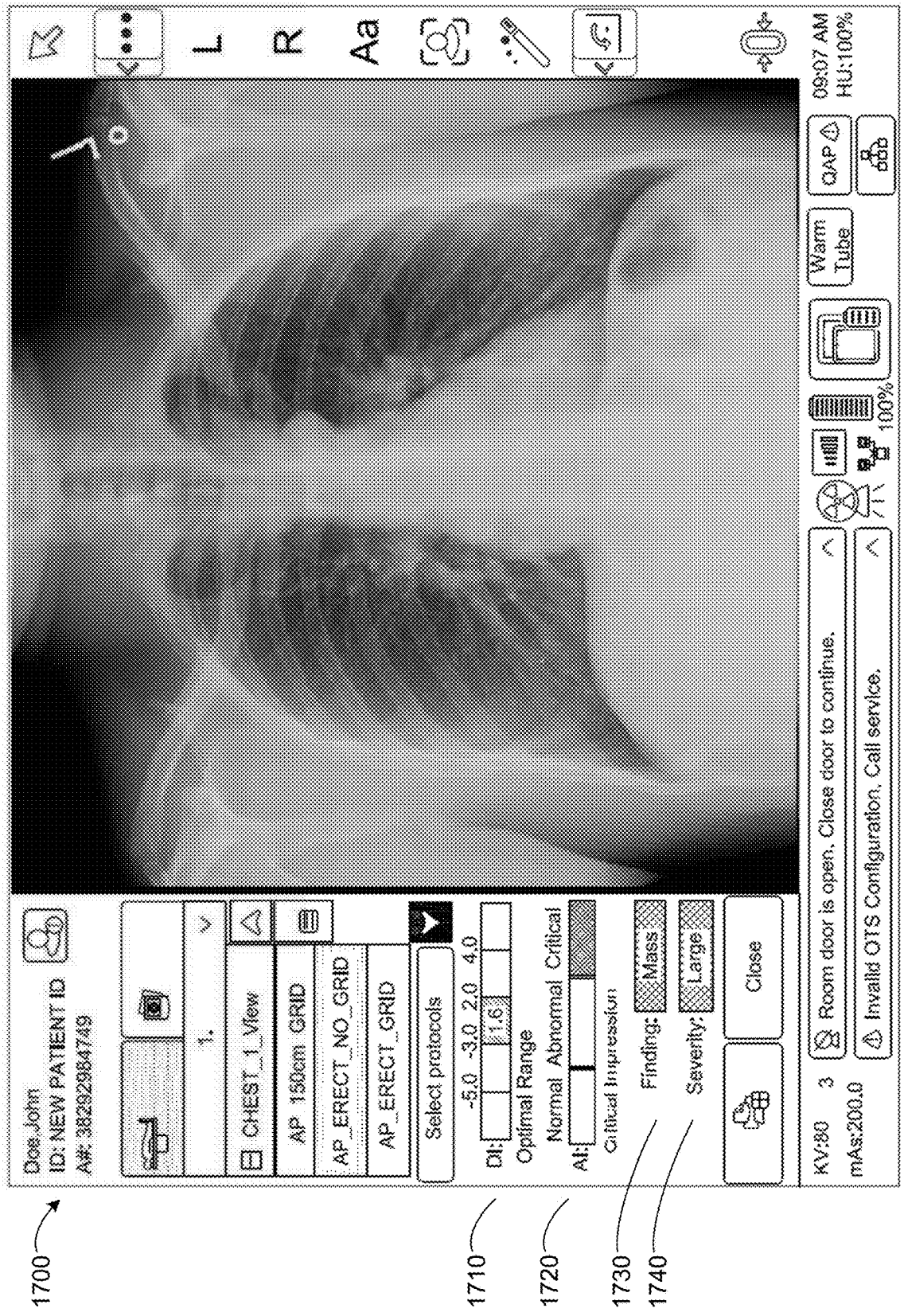
Figure 18:
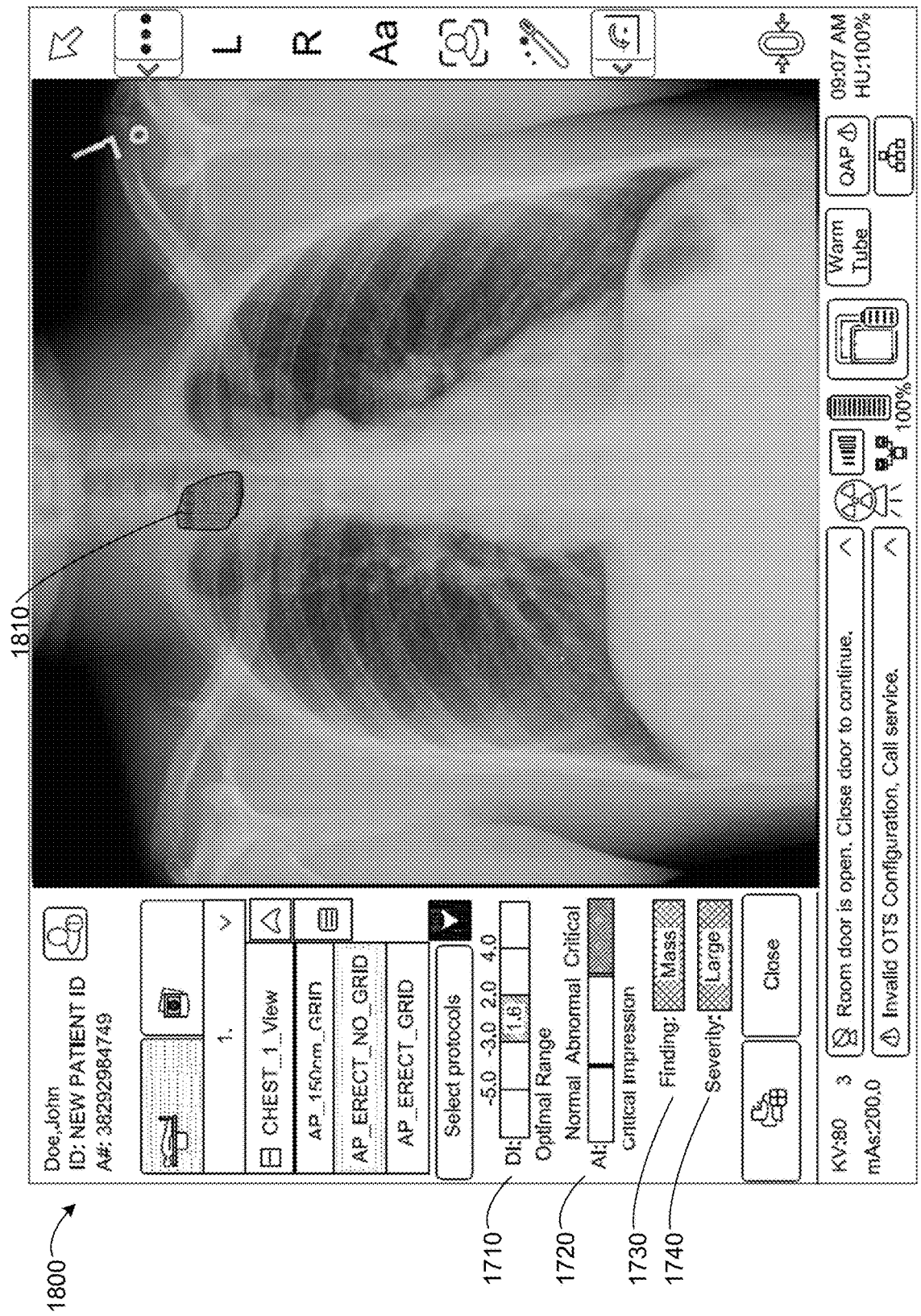

FIG. 17 illustrates another example GUI 1700, similar to but reduced from the example GUI 1600, including a DI 1710, a criticality impression 1720, an indication of finding 1730, and an indication of severity 1740. FIG. 18 illustrates an example GUI 1800 similar to the example GUI 1700 further including an overlay 1810 of the finding on the image.

Figure 19:
Figure 20:
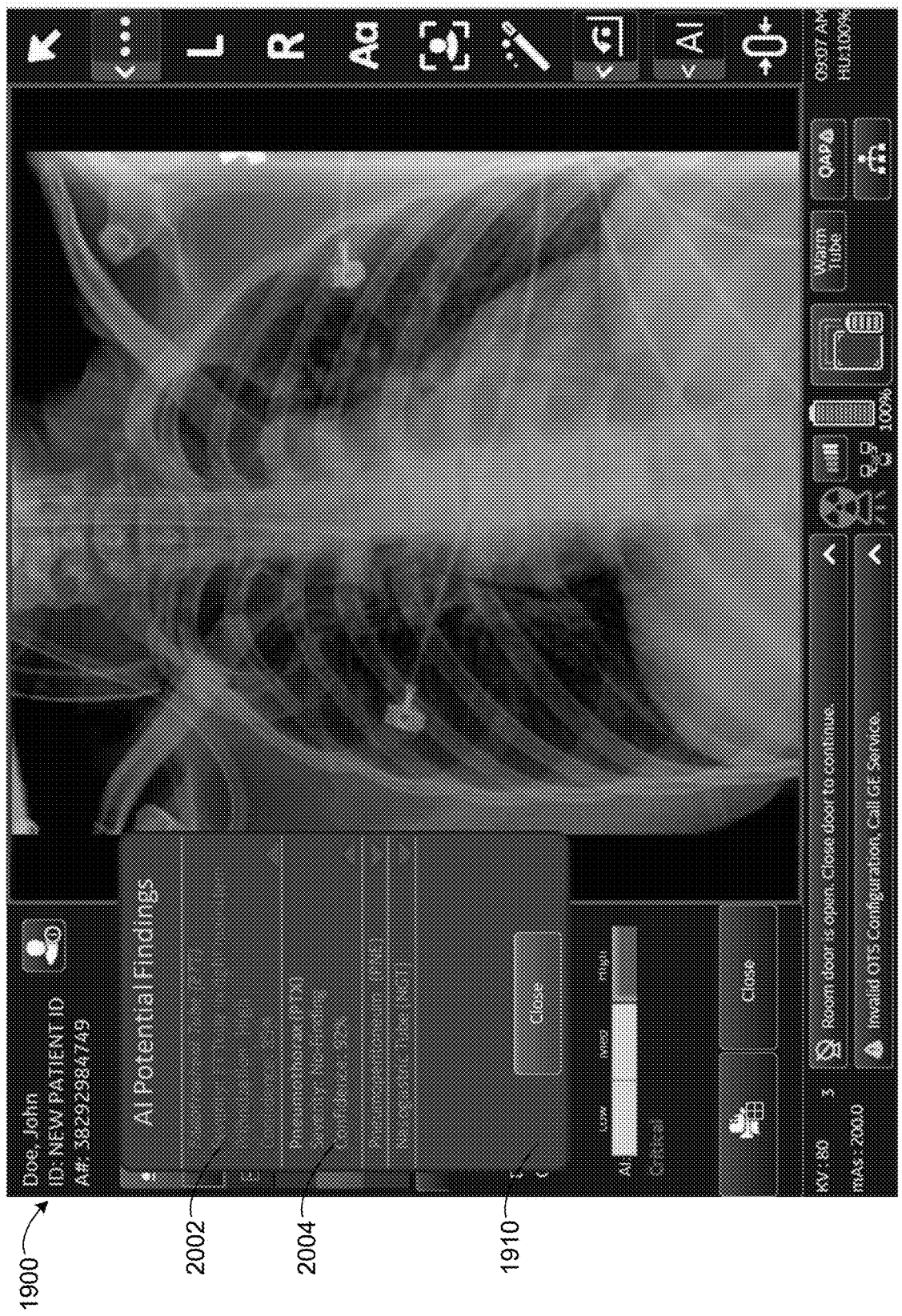
Figure 21:
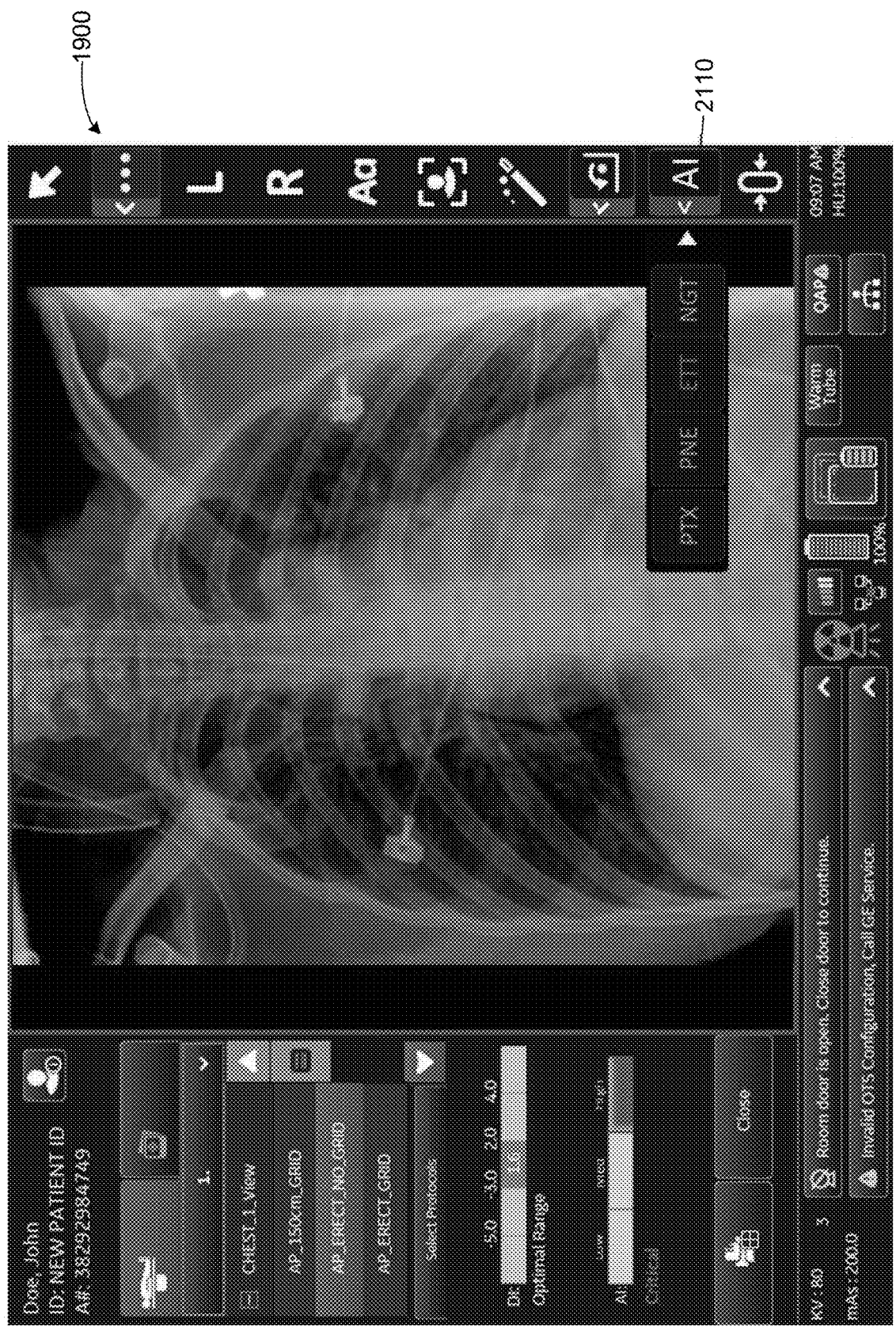

FIG. 19 illustrates an example GUI 1900 providing potential findings from AI in a window 1910 overlaid on the image viewer display of the GUI 1900. FIG. 20 illustrates another view of the example GUI 1900 in which entries 2002, 2004 in the AI findings window 1910 have been expanded to reveal further information regarding the respective finding 2002, 2004. FIG. 21 illustrates a further view of the example GUI 1900 in which the AI findings window 1910 has been reduced to a miniature representation 2110, selectable to view information regarding the findings.

Figure 22:
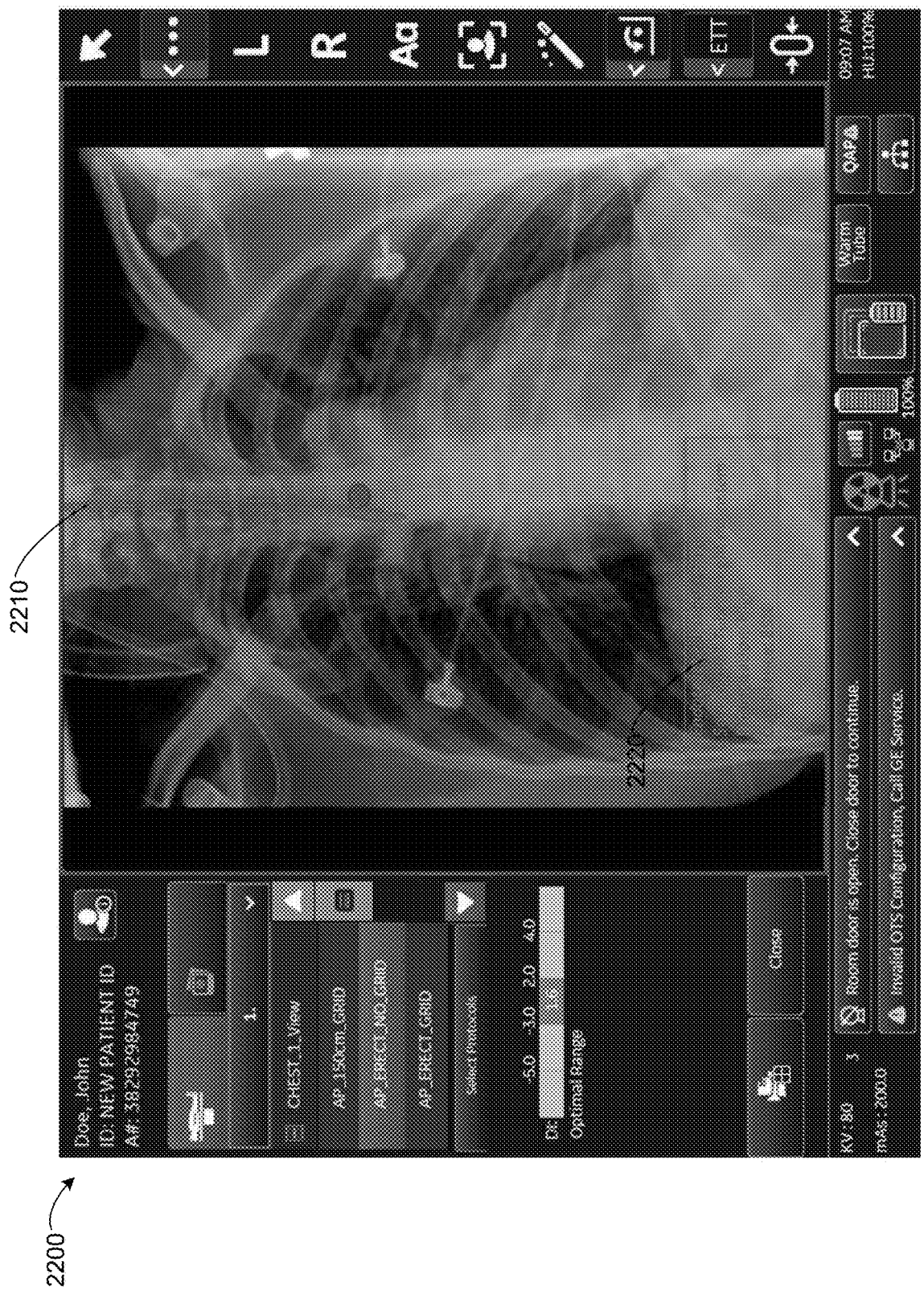
Figure 23:
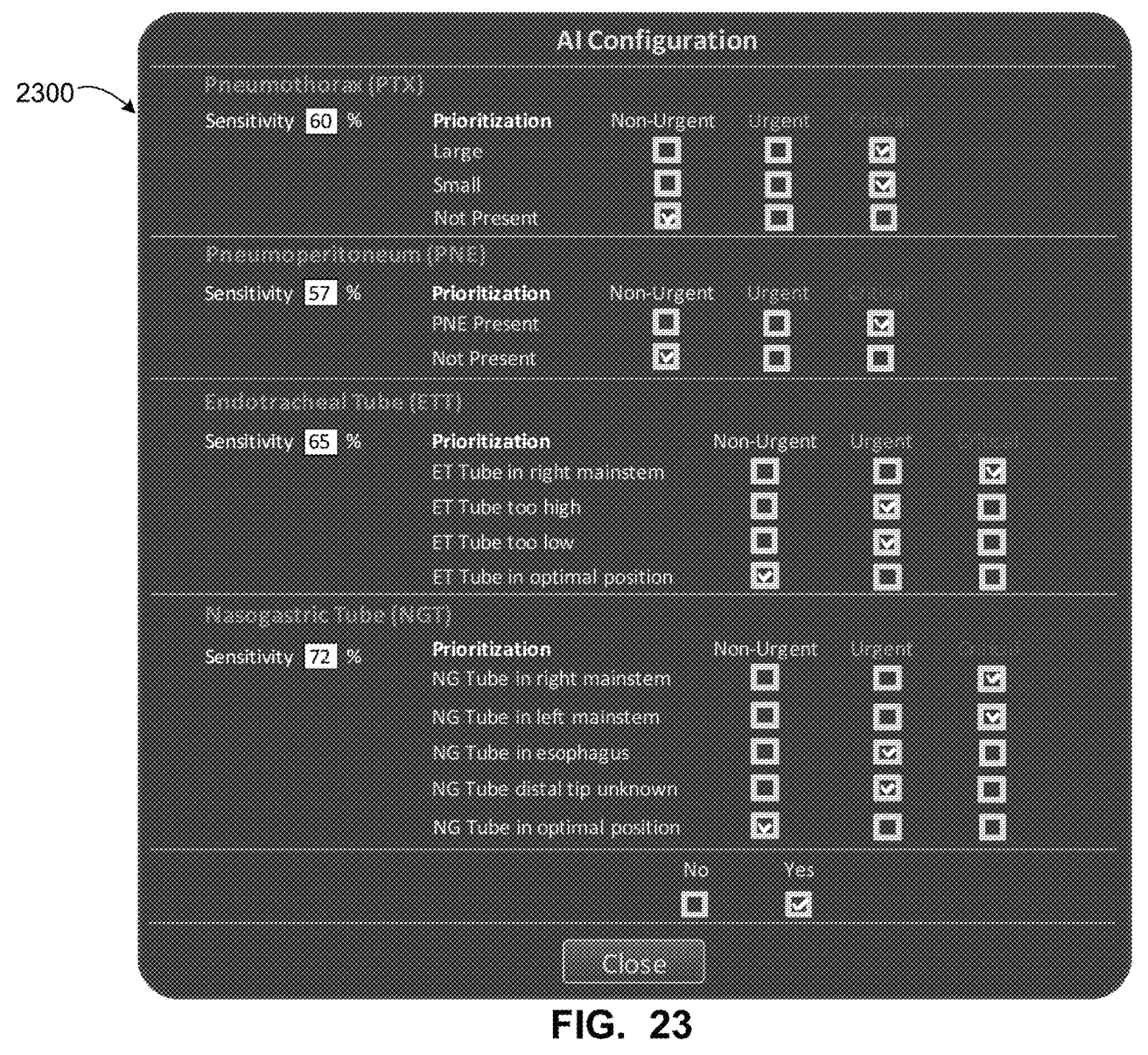

FIG. 22 illustrates an example GUI 2200 in which a finding 2210 is highlighted on an associated image, and related information 2220 is also displayed. FIG. 23 illustrates an example configuration interface 2300 to configure AI to process image and/or other data and generate findings.

Figure 24:
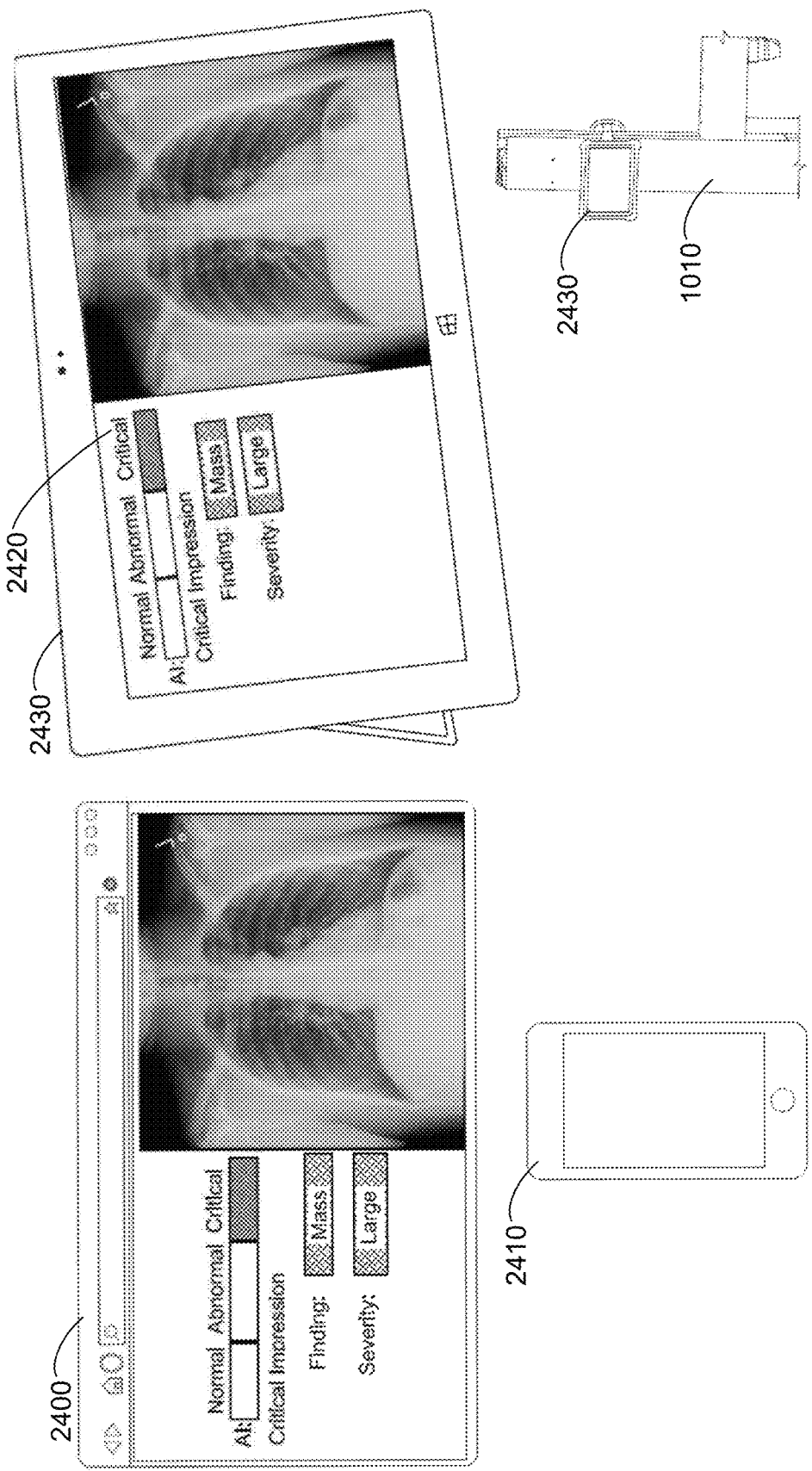

FIG. 24 illustrates a first example abbreviated GUI 2400 (e.g., a web-based GUI, etc.) displayable on a smartphone 2410 and/or other computing device, and a second abbreviated GUI 2420 shown on a tablet 2430. As shown in the example of FIG. 24, the tablet 2430 can be mounted with respect to the imaging device 10, 200, 1010 for viewing and interaction by an x-ray technician and/or other healthcare practitioner, for example.

Figure 25:
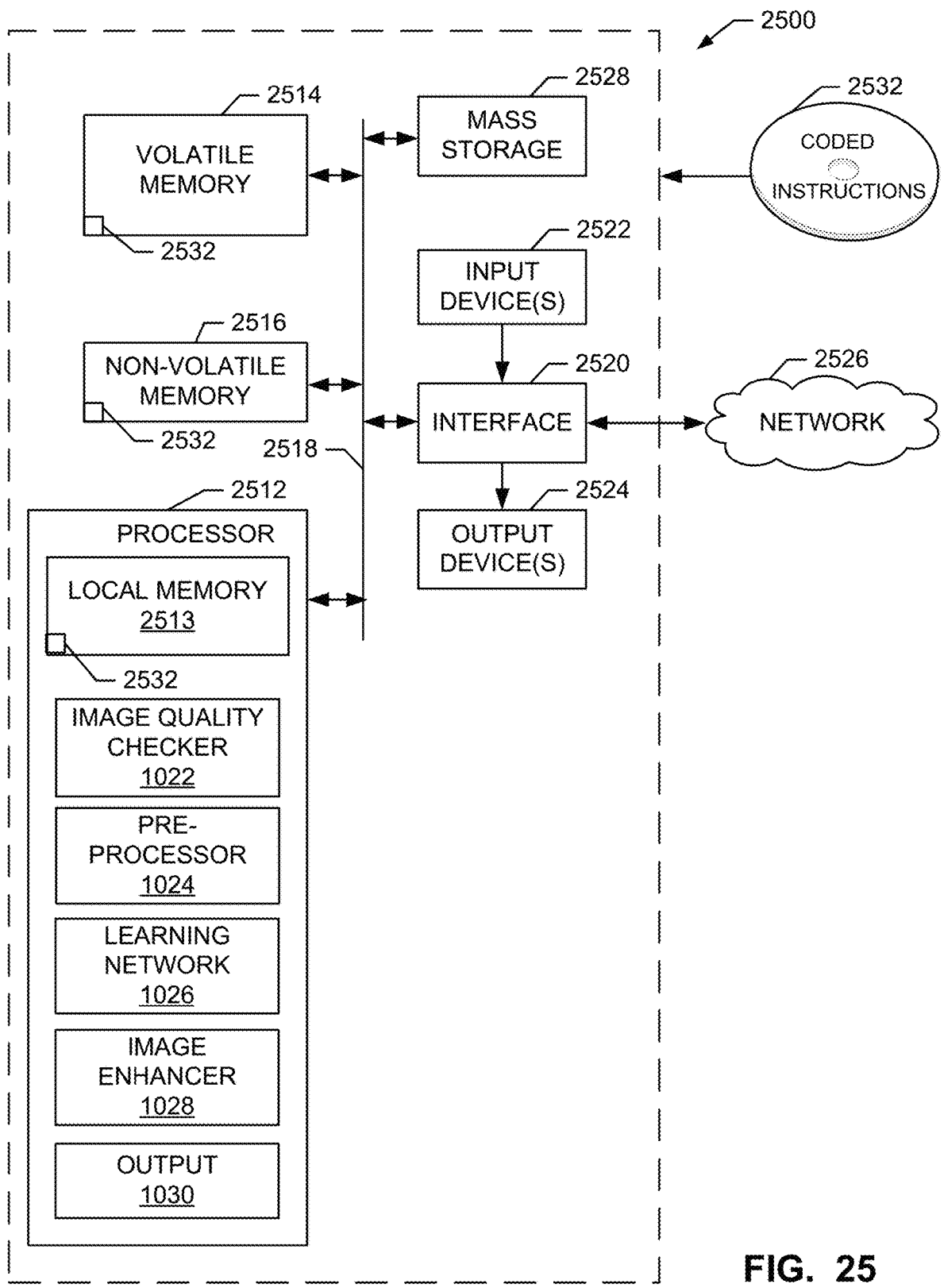
FIG. 25 is a block diagram of a processor platform structured to execute the example machine readable instructions to implement components disclosed and described herein.

FIG. 25 is a block diagram of an example processor platform 2500 structured to executing the instructions of at least FIGS. 11-12 to implement the example components disclosed and described herein. The processor platform 2500 can be, for example, a server, a personal computer, a mobile device (e.g., a cell phone, a smart phone, a tablet such as an iPad™), a personal digital assistant (PDA), an Internet appliance, or any other type of computing device.

The processor platform 2500 of the illustrated example includes a processor 2512. The processor 2512 of the illustrated example is hardware. For example, the processor 2512 can be implemented by integrated circuits, logic circuits, microprocessors or controllers from any desired family or manufacturer.

The processor 2512 of the illustrated example includes a local memory 2513 (e.g., a cache). The example processor 2512 of FIG. 25 executes the instructions of at least FIGS. 11-12 to implement the systems, infrastructure, displays, and associated methods of FIGS. 1-24 such as the image quality checker 1022, the pre-processor 1024, the learning network 1026, the image enhancer 1028, and the output 1030 of the processor 1020/2512, etc. The processor 2512 of the illustrated example is in communication with a main memory including a volatile memory 2514 and a non-volatile memory 2516 via a bus 2518. The volatile memory 2514 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 2516 may be implemented by flash memory and/or any other desired type of memory device. Access to the main memory 2514, 2516 is controlled by a clock controller.

The processor platform 2500 of the illustrated example also includes an interface circuit 2520. The interface circuit 2520 may be implemented by any type of interface standard, such as an Ethernet interface, a universal serial bus (USB), and/or a PCI express interface.

In the illustrated example, one or more input devices 2522 are connected to the interface circuit 2520. The input device(s) 2522 permit(s) a user to enter data and commands into the processor 2512. The input device(s) can be implemented by, for example, a sensor, a microphone, a camera (still or video, RGB or depth, etc.), a keyboard, a button, a mouse, a touchscreen, a track-pad, a trackball, isopoint and/or a voice recognition system.

One or more output devices 2524 are also connected to the interface circuit 2520 of the illustrated example. The output devices 2524 can be implemented, for example, by display devices (e.g., a light emitting diode (LED), an organic light emitting diode (OLED), a liquid crystal display, a cathode ray tube display (CRT), a touchscreen, a tactile output device, and/or speakers). The interface circuit 2520 of the illustrated example, thus, typically includes a graphics driver card, a graphics driver chip or a graphics driver processor.

The interface circuit 2520 of the illustrated example also includes a communication device such as a transmitter, a receiver, a transceiver, a modem and/or network interface card to facilitate exchange of data with external machines (e.g., computing devices of any kind) via a network 2526 (e.g., an Ethernet connection, a digital subscriber line (DSL), a telephone line, coaxial cable, a cellular telephone system, etc.).

The processor platform 2500 of the illustrated example also includes one or more mass storage devices 2528 for storing software and/or data. Examples of such mass storage devices 2528 include floppy disk drives, hard drive disks, compact disk drives, Blu-ray disk drives, RAID systems, and digital versatile disk (DVD) drives.

The coded instructions 2532 of FIG. 25 may be stored in the mass storage device 2528, in the volatile memory 2514, in the non-volatile memory 2516, and/or on a removable tangible computer readable storage medium such as a CD or DVD.

From the foregoing, it will be appreciated that the above disclosed methods, apparatus, and articles of manufacture have been disclosed to monitor, process, and improve operation of imaging and/or other healthcare systems using a plurality of deep learning and/or other machine learning techniques.

Thus, certain examples facilitate image acquisition and analysis at the point of care such as via a portable imaging device at the point of patient imaging. If images should be re-taken, further analysis done right away, and/or other criticality explored sooner, rather than later, the example systems, apparatus, and methods disclosed and described herein can facilitate such action to automate analysis, streamline workflow, and improve patient care.

Certain examples provide a specially-configured imaging apparatus that can acquire images and operate as a decision support tool at the point of care for a critical care team. Certain examples provide an imaging apparatus that functions as a medical device to provide and/or facilitate diagnosis at the point of care to detect radiological findings, etc. The apparatus can trigger a critical alert for a radiologist and/or critical care team to bring immediate attention to the patient. The apparatus enables patient triaging after the patient's exam, such as in a screening environment, wherein negative tests allow the patient to return home, while a positive test would require the patient to be seen by a physician before returning home In certain examples, a mobile device and/or cloud product enables a vendor-neutral solution, proving point of care alerts on any digital x-ray system (e.g., fully integrated, upgrade kit, etc.). In certain examples, embedded AI algorithms executing on a mobile imaging system, such as a mobile x-ray machine, etc., provide point of care alerts during and/or in real-time following image acquisition, etc.

By hosting AI on the imaging device, the mobile x-ray system can be used in rural regions without hospital information technology networks, or even on a mobile truck that brings imaging to patient communities, for example. Additionally, if there is long latency to send an image to a server or cloud, AI on the imaging device can instead be executed and generate output back to the imaging device for further action. Rather than having the x-ray technologist moved onto the next patient and the x-ray device no longer at the patient's bedside with the clinical care team, image processing, analysis, and output can occur in real time (or substantially real time given some data transfer/retrieval, processing, and output latency) to provide a relevant notification to the clinical care team while they and the equipment are still with or near the patient. For trauma cases, for example, treatment decisions need to be made fast, and certain examples alleviate the delay found with other clinical decision support tools.

Mobile X-ray systems travel throughout the hospital to the patient bedside (e.g., emergency room, operating room, intensive care unit, etc. Within a hospital, network communication may be unreliable in "dead" zones of the hospital (e.g., basement, rooms with electrical signal interference or blockage, etc.). If the X-ray device relies on building Wi-Fi, for example, to push the image to a server or cloud which is hosting the AI model and then wait to receive the AI output back to the X-ray device, then patient is at risk of not having reliability in critical alerts when needed. Further, if a network or power outage impacts communications, the AI operating on the imaging device can continue to function as a self-contained, mobile processing unit.

Examples of alerts generated for general radiology can include critical alerts (e.g., for mobile x-ray, etc.) such as pneumothorax, tubes and line placement, pleural effusion, lobar collapse, pneumoperitoneum, pneumonia, etc.; screening alerts (e.g., for fixed x-ray, etc.) such as tuberculosis, lung nodules, etc.; quality alerts (e.g., for mobile and/or fixed x-ray, etc.) such as patient positioning, clipped anatomy, inadequate technique, image artifacts, etc.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. A mobile imaging apparatus comprising:
wheels;
a source;
a detector; and
a housing including:
an image data store to store image data acquired at a location using the mobile imaging apparatus; and
at least one processor to facilitate acquisition of the image data and to process the image data acquired at the location according to an image quality measure, the image quality measure selected based on an analysis of at least one of digital imaging and communication in medicine (DICOM) header information or other DICOM metadata, the at least one processor to implement:
a trained learning network to process, when the image data satisfies the selected image quality measure, the image data while at the location to identify a clinical finding in the image data, the identification of a clinical finding to trigger a notification at the mobile imaging apparatus via an output to notify a healthcare practitioner regarding the clinical finding and prompt a responsive action with respect to a patient associated with the image data.

2. The apparatus of claim 1, wherein the at least one processor is to implement an image quality checker to evaluate the image data from the image data store in comparison to the image quality measure using an artificial intelligence model operating on the mobile imaging apparatus at the location.

3. The apparatus of claim 2, wherein the image quality checker selects the image quality measure based on the analysis of the at least one of the DICOM header information or other DICOM metadata.

4. The apparatus of claim 1, wherein the image quality measure includes analysis of at least one of DICOM header information or other DICOM metadata to confirm at least one of protocol or anatomy in the image data.

5. The apparatus of claim 1, wherein the mobile imaging apparatus is a mobile x-ray imaging apparatus.

6. The apparatus of claim 1, wherein the output includes a display, wherein the notification is output via a graphical user interface displayed via the display at the mobile imaging apparatus.

7. The apparatus of claim 6, wherein presentation of the notification corresponds to a criticality of the clinical finding.

8. The apparatus of claim 1, wherein the trained learning network includes a deep learning network trained on reference image data and associated findings and deployed to the mobile imaging apparatus.

9. The apparatus of claim 1, wherein the at least one processor is to implement a pre-processor to prepare the image data for processing by the trained learning network after evaluation according to the image quality measure.

10. The apparatus of claim 1, wherein the at least one processor is to implement an image enhancer to process the image data to enhance the clinical finding in a displayed image resulting from the image data.

11. A non-transitory computer-readable storage medium in a mobile imaging apparatus including wheels, a source, a detector, and a housing including the computer-readable storage medium and at least one processor, the computer-readable storage medium to store image data acquired at a location using the mobile imaging apparatus and to include instructions which, when executed, cause the at least one processor in the mobile imaging apparatus to at least facilitate acquisition of the image data and to process the image data acquired at the location according to an image quality measure, the image quality measure selected based on an analysis of at least one of digital imaging and communication in medicine (DICOM) header information or other DICOM metadata, the instructions, when executed, to cause the at least one processor to implement a trained learning network to process, when the image data satisfies the selected image quality measure, the image data while at the location to identify a clinical finding in the image data, the identification of a clinical finding to trigger a notification at the mobile imaging apparatus via an output to notify a healthcare practitioner regarding the clinical finding and prompt a responsive action with respect to a patient associated with the image data.

12. The non-transitory computer-readable storage medium of claim 11, wherein the instructions, when executed, cause the at least one processor to implement an image quality checker to evaluate the image data in comparison to the image quality measure using an artificial intelligence model operating on the mobile imaging apparatus at the location.

13. The non-transitory computer-readable storage medium of claim 12, wherein the image quality checker selects the image quality measure based on the analysis of the at least one of the DICOM header information or other DICOM metadata.

14. The non-transitory computer-readable storage medium of claim 11, wherein the image quality measure includes analysis of at least one of DICOM header information or other DICOM metadata to confirm at least one of protocol or anatomy in the image data.

15. The non-transitory computer-readable storage medium of claim 11, wherein the mobile imaging apparatus is a mobile x-ray imaging apparatus.

16. The non-transitory computer-readable storage medium of claim 11, wherein the output includes a display, wherein the notification is output via a graphical user interface displayed via the display at the mobile imaging apparatus.

17. The non-transitory computer-readable storage medium of claim 16, wherein presentation of the notification corresponds to a criticality of the clinical finding.

18. The non-transitory computer-readable storage medium of claim 11, wherein the trained learning network includes a deep learning network trained on reference image data and associated findings and deployed to the mobile imaging apparatus.

19. The non-transitory computer-readable storage medium of claim 11, wherein the instructions, when executed, cause the at least one processor to implement a pre-processor to prepare the image data for processing by the trained learning network after evaluation according to the image quality measure.

20. The non-transitory computer-readable storage medium of claim 11, wherein the instructions, when executed, cause the at least one processor to implement an image enhancer to process the image data to enhance the clinical finding in a displayed image resulting from the image data.

* * * * *